(12) United States Patent
Bertolero et al.

(10) Patent No.: US 7,542,807 B2
(45) Date of Patent: Jun. 2, 2009

(54) CONDUCTION BLOCK VERIFICATION PROBE AND METHOD OF USE

(75) Inventors: Arthur A. Bertolero, Danville, CA (US); Tamer Ibrahim, Pleasant Hill, CA (US); Steve Geyster, Milton, MA (US); Mathew Williams, New York, NY (US)

(73) Assignee: Endoscopic Technologies, Inc., Danville, CA (US)

( * ) Notice: Subject to any disclaimer, the term of this patent is extended or adjusted under 35 U.S.C. 154(b) by 338 days.

(21) Appl. No.: 11/186,149

(22) Filed: Jul. 20, 2005

(65) Prior Publication Data

US 2006/0015165 A1    Jan. 19, 2006

Related U.S. Application Data

(63) Continuation-in-part of application No. 10/988,021, filed on Nov. 12, 2004, now Pat. No. 7,399,300, which is a continuation-in-part of application No. 10/410,618, filed on Apr. 8, 2003, now Pat. No. 7,226,448, which is a continuation-in-part of application No. 10/272,446, filed on Oct. 15, 2002, now Pat. No. 6,849,075.

(60) Provisional application No. 60/337,070, filed on Dec. 4, 2001, provisional application No. 60/519,726, filed on Nov. 12, 2003.

(51) Int. Cl.
*A61N 1/04* (2006.01)
*A61N 1/05* (2006.01)

(52) U.S. Cl. .......................................... 607/119; 607/9

(58) Field of Classification Search .................... 607/9, 607/74
See application file for complete search history.

(56) References Cited

U.S. PATENT DOCUMENTS 3,949,759 A    4/1976    Brownlee et al.

(Continued)

OTHER PUBLICATIONS

Nicolet Biomedical, "Multi-Mode Program Puls (MMP Plus) User Guide", Part No. 269-570600, Jun. 2000.*

(Continued)

*Primary Examiner*—Carl H Layno
*Assistant Examiner*—Yun Haeng Lee
(74) *Attorney, Agent, or Firm*—GSS Law Group; James J. Leary; Carol D. Titus

(57) ABSTRACT

Devices and methods provide for ablation of cardiac tissue for treating cardiac arrhythmias such as atrial fibrillation. Although the devices and methods are often to be used to ablate epicardial tissue in the vicinity of at least one pulmonary vein, various embodiments may be used to ablate other cardiac tissues in other locations on a heart. Devices generally include at least one tissue contacting member for contacting epicardial tissue and securing the ablation device to the epicardial tissue, and at least one ablation member for ablating the tissue. Various embodiments include features, such as suction apertures, which enable the device to attach to the epicardial surface with sufficient strength to allow the tissue to be stabilized via the device. For example, some embodiments may be used to stabilize a beating heart to enable a beating heart ablation procedure.

4 Claims, 22 Drawing Sheets

U.S. PATENT DOCUMENTS

| | | | | |
|---|---|---|---|---|
| 4,805,616 | A | * | 2/1989 | Pao .............................. 606/50 |
| 5,222,501 | A | | 6/1993 | Ideker et al. |
| 5,323,781 | A | | 6/1994 | Ideker et al. |
| 5,895,386 | A | * | 4/1999 | Odell et al. ................... 606/50 |
| 5,954,662 | A | | 9/1999 | Swanson et al. |
| 6,064,906 | A | | 5/2000 | Langberg et al. |
| 6,070,100 | A | | 5/2000 | Bakels et al. |
| 6,223,079 | B1 | | 4/2001 | Bakels et al. |
| 6,231,571 | B1 | * | 5/2001 | Ellman et al. .................. 606/41 |
| 6,292,701 | B1 | * | 9/2001 | Prass et al. ................... 607/116 |
| 6,381,499 | B1 | * | 4/2002 | Taylor et al. ................. 607/118 |
| 6,502,576 | B1 | | 1/2003 | Lesh |
| 6,558,382 | B2 | | 5/2003 | Jahns et al. |
| 6,663,622 | B1 | | 12/2003 | Foley et al. |
| 6,679,269 | B2 | | 1/2004 | Swanson |
| 6,805,130 | B2 | * | 10/2004 | Tasto et al. .................. 128/898 |
| 2002/0068930 | A1 | * | 6/2002 | Tasto et al. ..................... 606/32 |

OTHER PUBLICATIONS

Sapp JL et al., 'Ablation lesion size correlates with pacing threshold: a physiological basis for use of pacing to assess ablation lesions', Pacing Clin Electrophysiol, Jul. 2004, vol. 27, No. 7, (abstract only) Medline. Division of Cardiology, Department of Medicine, QEII Health Sciences Centre, Dalhousie University, Halifax, Canada. PreMedline Identifier No. 0015271012.

Delacretaz E et al., 'Assessment of radiofrequency ablation effect from unipolar pacing threshold', Pacing Clin Electrophysiol, Oct. 2003, vol. 26, No. 10, (abstract only) Medline. Cardiac Arrhythmia Service and Clinical Electrophysiology Laboratory, Brigham and Women's Hospital, Harvard Medical School, Boston, Massachusetts 02115, USA. PreMedline Identifier No. 0014516340.

Roithinger FX et al., 'Low-power radiofrequency application and intracardiac echocardiography for creation of continuous left artial linear lesions', J Cardiovasc Electrophysiol, May 1999, vol. 10, No. 5 (abstract only), Medline. Department of Medicine and Cardiovascular Research Institute, University of California San Francisco, 94143-1354, USA. PreMedline Identifier No. 0010355924.

Sanchez JE et al., 'Identification of transmural necrosis along a linear catheter ablation lesion during atrial fibrillation and sinus rhythm', J Cardiovasc Electrophysiol, Feb. 2003, vol. 8, No. 1, (abstract only), Medline. Deparation of Internal Medicine, Devisional of Cardiovascular Diseases, Cardiac Rhythm Management Laboratory, University of Alabama at Birmingham, Birmingham, AL 35294, USA. PreMedline Identifier No. 0012652172.

Shake JG et al., 'Transmural atrial insulating lesions using epicardially applied radiofrequency energy coupled with saline irrigation', J invest Surg, Mar.-Apr. 2002, vol. 15, No. 2 (abstract only), Medline. Department of Surgery, Division of Cardiovascular Surgery, University of Minnesota, Minneapolis, USA. PreMedine Identifier No. 0012028620.

Jumrissirikul P et al., 'Prospective comparison of lesions created using a multipolar microcatheter ablation system with those created using a pullback approach with standard radiofrequency ablation in the canine atrium', Pacting Clin Electrophysiol, Feb. 2000, vol. 23, No. 2 (abstract only), Medline. Department of Medicine, Johns Hopkins Medical Institutions, Baltimore, Maryland, USA. PreMedine Identifier No. 0010709228.

Avitall B et al., 'The creation of linear contiguous lesions in the atria with an expandable loop catheter', J Am Coll Cadiol, Mar. 15, 1999, vol. 33, No. 4 (abstract only), Medline. Section of Cardiology, University of Illinois at Chicago, 60612, USA. PreMedine Identifier No. 0010091824.

Avitall B et al., 'New cryotechnology for electrical isolation of the pulmonary veins', J Cardiovasc Electrophysiol, Mar. 2003, vol. 14, No. 3 (abstract only), Medline. Department of Medicine, University of Illinois at Chicago, 60612, USA. PreMedine Identifier No. 0012716111.

Van Rensburg H. et al., 'Simulatneous creation and evaluation of linear radiofrequency lesions'. J Interv Card Electrophysiol, Jul. 2002, vol. 6, No. 3 (abstract only), Medline. Department of Cardiology, University Hospital Gasthuisberg, University of Leuven, Leuven, Belgium. PreMedine Identifier No. 0012154323.

Liem LB et al., 'Electrophysiological correlates of transmural linear ablation'. Pacing Clin Electrophysiol, Jan. 2000, vol. 23, No. 1 (abstract only), Medline. Stanford University, California. PreMedine Identifier No. 0010666752.

Ndrepepa G. et al., 'Acute electrophysiologic effects and antifibrillatory actions of the long linear lesions in the right atrium in a sheep model'. J Interv Card Electrophysiol, Oct. 2000, vol. 4, No. 3 (abstract only), Medline. Universitat Munchen, Munich, Germany. PreMedine Identifier No. 0011046192.

Chorro FJ et al., 'Acute effects of radiofrequency ablation upon atrial conduction in proximity to the lesion site'. Pacing Clin Electrophysiol, Apr. 1998, vol. 21, No. 4 Pt. 1 (abstract only), Medline. Service of Cardiology, Valencia University Clinic Hospital, Spain. PreMedine Identifier No. 0009584295.

Wu G, 'Experimental study of laser ablation on lethal arrhythmias in dogs'. Zhonghua Xin Xue Guan Bing Za Zhi, Apr. 1991, vol. 19, No. 2 (abstract only) Medline. Cardiovascular Institute, Chinese Academy of Medical Sciences, Beijing. PreMedine Identifier No. 0001879315.

'Pacemakers' [online]. History of Cardiac Surgery, [retrieved on Feb. 15, 2006] Retrieved from the Internet: http://www.ctsnet.org/edmunds/Chapter1section14.html.

* cited by examiner

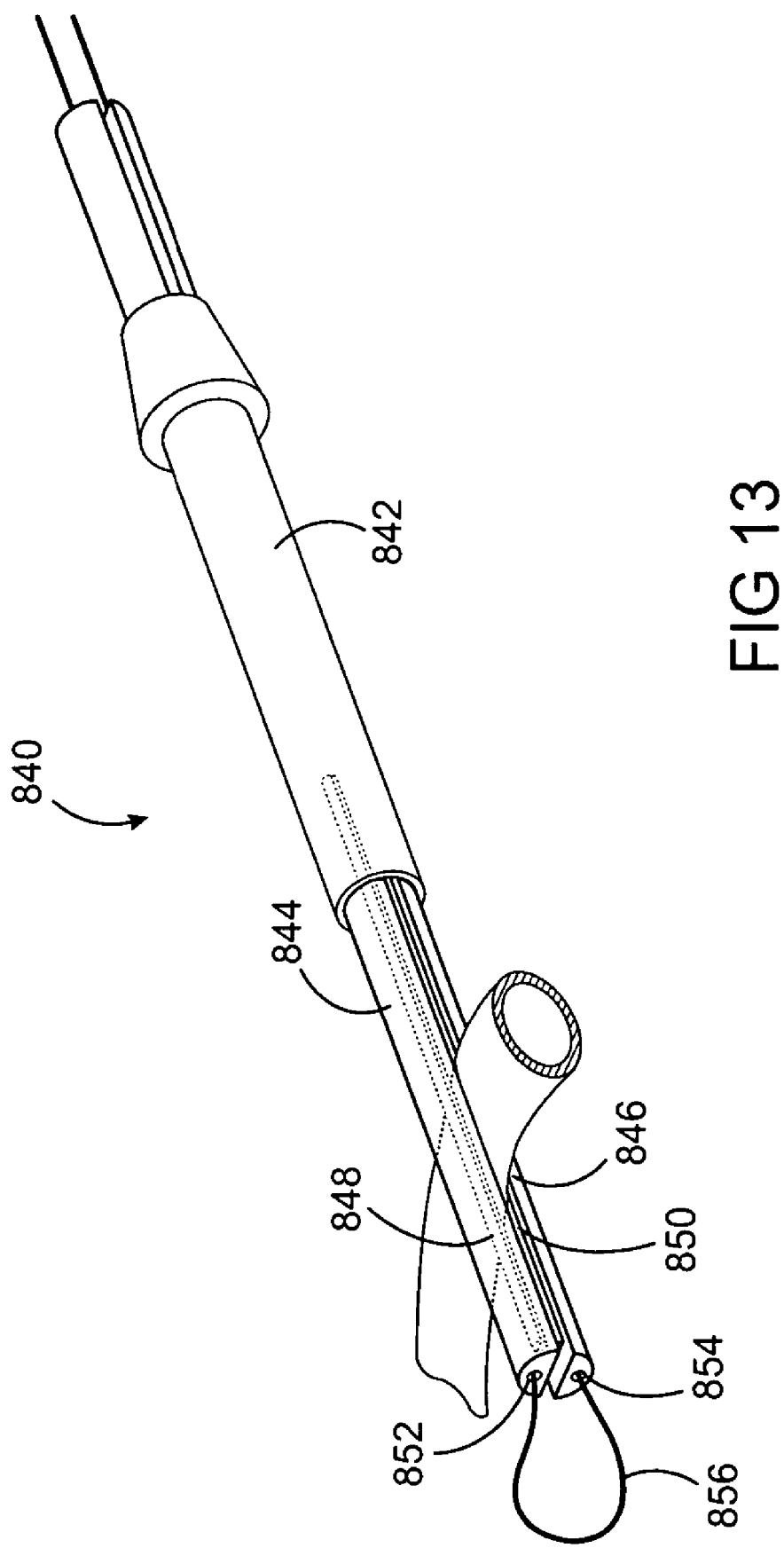

CONDUCTION BLOCK VERIFICATION PROBE AND METHOD OF USE

CROSS-REFERENCES TO RELATED APPLICATIONS

The present application is a continuation-in-part application which claims priority of U.S. patent application Ser. No. 10/988,021, which was filed on Nov. 12, 2004, U.S. Pat. No. 7,399,300 which is a continuation-in-part application which claims priority of U.S. patent application Ser. No. 10/410,618, which was filed on Apr. 8, 2003, now U.S. Pat. No. 7,226,448 which is a continuation-in-part of and claims priority of U.S. patent application Ser. No. 10/272,446, which was filed Oct. 15, 2002, now U.S. Pat. No. 6,849,075 which claims priority to U.S. Provisional Patent Application Ser. No. 60/337,070, filed Dec. 4, 2001, entitled "Methods and Devices for the Least Invasive Cardiac Surgery of Atrial Fibrillation." U.S. patent application Ser. No. 10/988,021 also claims the priority to U.S. Provisional Patent Application Ser. No. 60/519,726, filed Nov. 12, 2003, entitled "Ablation Device." The entire contents of these applications are hereby incorporated by reference.

BACKGROUND OF THE INVENTION

The present invention relates generally to medical devices and methods. More specifically, the invention relates to devices and methods to verify electrical conduction block across ablation lesions in cardiac tissue. The invention also relates to devices and methods for ablating epicardial tissue to treat cardiac arrhythmias such as atrial fibrillation.

Atrial fibrillation (AF) is a heart beat rhythm disorder (or "cardiac arrhythmia") in which the upper chambers of the heart known as the atria quiver rapidly instead of beating in a steady rhythm. This rapid quivering reduces the heart's ability to properly function as a pump. AF is characterized by circular waves of electrical impulses that travel across the atria in a continuous cycle. It is the most common clinical heart arrhythmia, affecting more than two million people in the United States and some six million people worldwide.

Atrial fibrillation typically increases the risk of acquiring a number of potentially deadly complications, including thrombo-embolic stroke, dilated cardiomyopathy and congestive heart failure. Quality of life is also impaired by common AF symptoms such as palpitations, chest pain, dyspnea, fatigue and dizziness. People with AF have, on average, a five-fold increase in morbidity and a two-fold increase in mortality compared to people with normal sinus rhythm. One of every six strokes in the U.S. (some 120,000 per year) occurs in patients with AF, and the condition is responsible for one-third of all hospitalizations related to cardiac rhythm disturbances (over 360,000 per year), resulting in billions of dollars in annual healthcare expenditures.

AF is the most common arrhythmia seen by physicians, and the prevalence of AF is growing rapidly as the population ages. The likelihood of developing AF increases dramatically as people age; the disorder is found in about 1% of the adult population as a whole, and in about 6% of those over age 60. By age 80, about 9% of people (one in 11) will have AF. According to a recent statistical analysis, the prevalence of AF in the U.S. will more than double by the year 2050, as the proportion of elderly increases. A recent study called The Anticoagulation and Risk Factors in Atrial Fibrillation (ATRIA) study, published in the Spring of 2001 in the Journal of the American Medical Association (JAMA), found that 2.3 million U.S. adults currently have AF and this number is likely to increase over the next 50 years to more than 5.6 million, more than half of whom will be age 80 or over.

As the prevalence of AF increases, so will the number of people who develop debilitating or life-threatening complications, such as stroke. According to Framingham Heart Study data, the stroke rate in AF patients increases from about 3% of those aged 50-59 to more than 7% of those aged 80 and over. AF is responsible for up to 35% of the strokes that occur in people older than age 85.

Efforts to prevent stroke in AF patients have so far focused primarily on the use of anticoagulant and antiplatelet drugs, such as warfarin and aspirin. Long-term warfarin therapy is recommended for all AF patients with one or more stroke risk factors, including all patients over age 75. Studies have shown, however, that warfarin tends to be under-prescribed for AF. Despite the fact that warfarin reduces stroke risk by 60% or more, only 40% of patients age 65-74 and 20% of patients over age 80 take the medication, and probably fewer than half are on the correct dosage. Patient compliance with warfarin is problematic, and the drug requires vigilant blood monitoring to reduce the risk of bleeding complications.

Electrophysiologists classify AF by the "three Ps": paroxysmal, persistent, or permanent. Paroxysmal AF—characterized by sporadic, usually self-limiting episodes lasting less than 48 hours—is the most amenable to treatment, while persistent or permanent AF is much more resistant to known therapies. Researchers now know that AF is a self-perpetuating disease and that abnormal atrial rhythms tend to initiate or trigger more abnormal rhythms. Thus, the more episodes a patient experiences and the longer the episodes last, the less chance of converting the heart to a persistent normal rhythm, regardless of the treatment method.

AF is characterized by circular waves of electrical impulses that travel across the atria in a continuous cycle, causing the upper chambers of the heart to quiver rapidly. At least six different locations in the atria have been identified where these waves can circulate, a finding that paved the way for maze-type ablation therapies. More recently, researchers have identified the pulmonary veins as perhaps the most common area where AF-triggering foci reside. Technologies designed to isolate the pulmonary veins or ablate specific pulmonary foci appear to be very promising and are the focus of much of the current research in catheter-based ablation techniques.

Although cardiac ablation devices and methods are currently available, many advances may still be made to provide improved devices and methods for ablating-epicardial tissue to treat AF and other arrhythmias. For example, currently available devices can be difficult to position and secure on epicardial tissue to perform an ablation. Devices such as bipolar ablation clamps and others can ablate tissue only in very limited patterns, such as one or two straight lines. Ablation devices often have no means for shielding ablative energy, to avoid unwanted burning of tissues in the vicinity of the heart, such as the esophagus. Relatively few devices can be secured to epicardial tissue with sufficient force to allow for stabilization of the heart. And many ablation devices may not be introduced by minimally invasive means, thus requiring an open surgical procedure. Typically, therefore, current cardiac ablation procedures for AF treatment still require stopping the heart and using a cardiopulmonary bypass apparatus.

Therefore, a need exists for improved devices and methods for ablating epicardial tissue to treat AF and other cardiac arrhythmias. Preferably, such devices and methods would provide ablation adjacent to and/or encircling one or more pulmonary veins, to disrupt conduction pathways and thus partially or completely treat AF. Also preferably, such devices and methods would allow for minimally invasive ablation procedures, in some cases on a beating heart. Such devices might also provide additional advantages, such as advantageous ablation patterns, shielding of ablative energy and/or the like. At least some of these objectives will be met by the present invention.

BRIEF SUMMARY OF THE INVENTION

Devices and methods of the present invention provide for ablation of cardiac tissue for treating cardiac arrhythmias such as atrial fibrillation. Although the devices and methods are often used to ablate epicardial tissue in the vicinity of at least one pulmonary vein, various embodiments may be used to ablate other cardiac tissues in other locations on a heart. Generally, devices of the invention include a tissue contacting member for contacting a portion of the epicardial tissue of a heart and securing the ablation device to the epicardial tissue, and an ablation member for ablating at least a portion of the tissue. In various embodiments, the devices have features which enable the device to attach to the epicardial surface with sufficient strength to allow the tissue to be stabilized via the device. For example, some embodiments may be used to stabilize a beating heart to enable a beating heart ablation procedure. Many of the devices may be introduced into a patient via minimally invasive incisions, introducer devices and the like. Although much of the following description focuses on using devices and methods of the invention to treat atrial fibrillation (AF) by ablating epicardial tissue on a human heart, the devices and methods may be used in veterinary or research contexts, to treat various heart conditions other than atrial fibrillation and/or to ablate cardiac tissue other than the epicardium.

In one aspect, a system for treating heart tissue to treat a cardiac arrhythmia comprises: at least one energy transmission member for applying energy to the heart tissue in a pattern to treat the cardiac arrhythmia; at least one tissue securing member coupled with the at least one energy transmission member for enhancing contact of the energy transmission member with the heart tissue; and at least one guiding member coupled with at least one of the energy transmission member and the tissue securing member for guiding the energy transmission member and the tissue securing member to a location for treating the heart tissue.

Optionally, such as system may further include at least one visualization member for enhancing visualization of the heart tissue and the treatment location. In some embodiments, for example, the visualization member may include an optic imaging device, a thermal imaging device, an ultrasound device, an electrical imaging device, a Doppler imaging device or the like, though any suitable device may be used. In some embodiments, an optic imaging device comprises a fiber optic device positionable to view a posterior portion of the heart tissue. In other embodiments, a thermal imaging device measures at least one heat transfer coefficient of the heart tissue to determine at least one of a type and a thickness of the heart tissue. In still other embodiments, an electrical imaging device measures electrical resistance and/or impedance of the heart tissue to determine a type and/or a thickness of the heart tissue.

In some embodiments, the at least one visualization member is removably coupled with at least one of the at least one energy transmission member, the at least one tissue securing member and the at least one guiding member. Also in some embodiments, the at least one visualization member may comprise at least one optic member for acquiring optic signals of an area to be visualized, and wherein the visualization member includes at least one inflatable member coupled with the visualization member at or near the optic member. For example, the inflatable member may provide a space in a body cavity and/or between at least two body tissues to enhance operation of the optic member. In some embodiments, the inflatable member includes an inflation port in fluid communication with an inflation lumen coupled with the visualization member for allowing introduction of a liquid or a gas to inflate the inflatable member. In some embodiments, the inflatable member reduces motion of the heart tissue when applied to the heart tissue.

Some embodiments of the invention also include at least one positioning device for contacting the heart tissue and positioning the heart tissue for treatment. For example, the positioning device may comprise a suction positioning device. In some embodiments, the positioning device reduces motion of a beating heart to further position the heart tissue for treatment.

The energy applied to the heart tissue may be any suitable energy, such as but not limited to radio frequency energy, ultrasound energy, microwave energy, cryogenic energy, thermoelectric energy and laser energy. In some embodiments, optionally, the energy transmission member contacts an epicardial surface of the heart tissue to transmit the energy, and wherein the energy is transmitted from the epicardial surface through the heart tissue to an endocardial surface. Sometimes, the energy is further transmitted through at least one of fat and connective tissue covering at least part of the epicardial surface. Some embodiments also include at least one grounding device for dispersing the energy from a patient undergoing an energy transmission heart procedure. Some embodiments may also include at least one needle coupled with the energy transmission member for insertion into the heart tissue to enhance the application of energy to the heart tissue. In some of these embodiments, the energy is transmitted from a tip of each needle. Optionally, the needle may be retractable. In some embodiments, for example, the retractable needle is exposed and retracted via a pneumatic member coupled with the energy transmission member. In some embodiments, the retractable needle is exposed and retracted automatically when the energy transmission member contacts the heart tissue. Also in some embodiments, the depth of penetration of the retractable needle into the heart tissue is adjustable.

Some embodiments may also include at least one closed circuit feedback loop for measuring and regulating operation of the energy transmission member. In some embodiments, either the energy transmission member or the tissue securing member further comprises at least one fluid aperture for applying fluid to the heart tissue to enhance the application of energy to the heart tissue.

In some embodiments, the energy transmission member is coupled with at least one guiding member such that a change in shape of the guiding member causes a corresponding change in shape of the energy transmission member. For example, the guiding member may comprise a deformable linear member, its shape being adjustable by a user, and wherein the energy transmission member comprises a deformable linear member coaxially coupled with the guiding member so as to move with the guiding member. In some embodiments, the guiding member is adjustable to at least partially encircle at least one pulmonary vein.

In some embodiments, the tissue securing member includes at least one connector for removably coupling with the at least one energy transmission member. Sometimes, the tissue securing member is conformable to a surface topography of the heart tissue. In various embodiments, a first longitudinal axis of the tissue securing member and a second longitudinal axis of the removably coupled energy transmission member may be collinear, parallel to one another or offset from one another. In some embodiments, the energy transmission member comprises a linear member, and the connector comprises a plurality of connectors disposed along a length of the tissue securing member for removably coupling the linear member with the tissue securing member. The tissue securing member may allow compressive force to be applied between the at least one energy transmission member and the heart tissue.

In some embodiments, the tissue securing member comprises at least one vacuum applying member. The vacuum applying member may comprise, for example: at least one vacuum lumen; at least one vacuum port in fluid communication with the lumen for coupling the lumen with a vacuum source; and at least one aperture in fluid communication with the lumen for applying vacuum force to the heart tissue. In some embodiments, the vacuum lumen comprises multiple, separate lumens, and each separate lumen is in fluid communication with a separate vacuum port. Such embodiments may optionally further include means for selectively applying vacuum to one or more of the separate lumens without applying vacuum to one or more other separate lumens. Alternatively or in addition, the apparatus may be provided with suction pod plugs that serve to occlude one or more of the suction apertures so that suction is applied only through the remaining suction apertures that have not been occluded with a suction pod plug.

In other embodiments, the tissue securing member comprises at least one expansible balloon member. The expansible balloon member may include at least one fluid introduction port for allowing introduction of a liquid or a gas to expand the balloon member. Some embodiments include multiple, separate balloon members, wherein each separate balloon member is in fluid communication with a separate fluid introduction port. Such embodiments may also include means for selectively introducing fluid into one or more of the separate balloons without introducing fluid into one or more other separate balloons. Optionally, in some embodiments, the tissue securing member prevents a portion of the heart tissue from being treated by the at least one energy transmission member. For example, the tissue securing member may comprise at least one insulation material for preventing the portion of the heart tissue from being treated. In one embodiment, the insulation material further prevents the at least one energy transmission member from contacting or harming other, non-cardiac tissue of the patient and from contacting or harming a user of the energy transmission member.

In some embodiments, the guiding member comprises at least one of an elongate shaft, a steerable guidewire and an introducer sheath. For example, the steerable guidewire may comprise a pushable guidewire having at least one relatively stiff portion and one relatively flexible portion for positioning the energy transmission member in a location for treatment. For example, the steerable guidewire may comprise a pullable guidewire to which tension is applied to steer the guidewire to position the energy transmission member in a location for treatment.

In another aspect, a system for treating heart tissue to treat a cardiac arrhythmia comprises: at least one therapeutic agent transmission member for applying at least one therapeutic agent to the heart tissue in a pattern to treat the cardiac arrhythmia; at least one tissue securing member coupled with the at least one energy transmission member for enhancing contact of the energy transmission member with the heart tissue; and at least one guiding member coupled with at least one of the energy transmission member and the tissue securing member for guiding the energy transmission member and the tissue securing member to a location for treating the heart tissue. In some embodiments, for example, the therapeutic agent transmission member comprises at least one lumen and at least one aperture in the lumen for allowing passage of the at least one therapeutic agent out of the lumen to contact the heart tissue.

Optionally, such a system may further include at least one needle coupled with the therapeutic agent transmission member for insertion into the heart tissue to enhance application of the at least one therapeutic agent to the heart tissue. The therapeutic agent transmission member itself may comprise at least one needle and at least one aperture adjacent a tip of each needle for allowing passage of the at least one therapeutic agent out of the needle to contact the heart tissue. Optionally, the needle may be retractable. For example, the retractable needle may be exposed and retracted via a pneumatic member coupled with the therapeutic agent transmission member. In some embodiments, the retractable needle is exposed and retracted automatically when the therapeutic agent transmission member contacts the heart tissue. Also in some embodiments, a depth of penetration of the retractable needle into the heart tissue is adjustable.

In another aspect of the invention, a method for treating heart tissue of a patient to treat a cardiac arrhythmia involves: advancing at least one treatment member coupled with at least one tissue securing member through an incision on the patient; visualizing a treatment area in the patient with at least one visualization member; contacting the heart tissue of the patient with the treatment member and the tissue securing member; applying a force, through the tissue securing member, to enhance contact of the treatment member with the heart tissue; and treating the heart tissue, using the at least one treatment member. In some embodiments, the treatment member and/or the tissue securing member are advanced through a port applied to the patient, the port having a diameter no greater than 5 cm.

In some embodiments, the advancing step includes guiding the treatment member and/or the tissue securing member using at least one guiding member. Guiding may involve, for example, using a pushable guidewire having at least one relatively stiff portion and one relatively flexible portion for positioning the treatment member in a location for treatment. Alternatively, guiding may involve using a pullable guidewire to which tension is applied to steer the guidewire to position the treatment member in a location for treatment.

Some embodiments of the method further include using at least one positioning device to position the heart tissue for treatment. This may involve, for example, applying suction to the heart tissue. In some embodiments, using the positioning device reduces motion of the heart tissue. In other embodiments, contacting the heart tissue comprises applying a suction force with the tissue securing member to increase a contact surface area of the tissue securing member with the heart tissue. Applying the suction force may further comprise providing consistent contact force between the heart tissue and the tissue securing member. Optionally, applying the suction force may comprise securing the tissue securing member and the treatment member to the heart tissue, the tissue securing member and the treatment member having the same cross-sectional shape.

In some embodiments, treating the heart tissue comprises applying energy to the heart tissue in a pattern to reduce or eliminate the cardiac arrhythmia. The applied energy may be in any suitable form, such as radio frequency energy, ultrasound energy, microwave energy, cryogenic energy, thermoelectric energy or laser energy. In some embodiments, the energy is applied to an epicardial surface of the heart, wherein the energy is transmitted from the epicardial surface through the heart tissue to an endocardial surface. Optionally, the energy may be further transmitted through fat and/or connective tissue covering at least part of the epicardial surface. Some methods may further include dispersing the energy from the patient through at least one grounding device coupled with the patient.

Some embodiments further involve inserting at least one needle into the heart tissue to enhance the application of energy to the heart tissue. For example, the energy may transmitted from a tip of each needle. Some methods include extending the at least one needle from a retracted position before applying the energy and retracting the at least one needle to the retracted position when the energy has been applied. Such methods may also include selecting a depth of penetration of the at least one retractable needle into the heart tissue. Other embodiments may involve measuring the application of energy to the heart tissue using at least one closed circuit feedback loop and regulating the application of energy to the heart tissue based on the measurement. Still other embodiments may include applying fluid to the heart tissue to enhance the application of energy to the heart tissue.

In alternative embodiments, treating the heart tissue comprises applying at least one therapeutic agent to the heart tissue in a pattern to reduce or eliminate the cardiac arrhythmia. For example, applying the at least one therapeutic agent may involve infusing the agent through at least one aperture in the at least one treatment member. In some embodiments, the therapeutic agent is infused through at least one aperture in at least one needle coupled with the treatment member. In some embodiments, applying the at least one therapeutic agent comprises inserting at least one needle into the heart tissue to a desired depth, injecting the at least one agent into the heart tissue, and removing the at least one needle from the heart tissue. Such a method may further include extending the at least one needle from a retracted position for insertion into the heart tissue and retracting the at least one needle to the retracted position after injection.

Yet another embodiment may include adjusting a shape of a guiding member coupled with the at least one treatment member to alter the shape of the treatment member. In some embodiments, adjusting the shape of the guiding member allows the treatment member to conform to a surface of the heart tissue. Also in some embodiments, adjusting the shape of the guiding member allows the treatment member to at least partially encircle at least one pulmonary vein. Some embodiments may also include removably coupling the tissue securing member with the at least one treatment member. Some embodiments may further include conforming the tissue securing member to a surface topography of the heart tissue.

In some embodiments, applying force comprises applying compressive force between the at least one treatment member and the heart tissue. Applying the compressive force, in turn, may comprise applying vacuum force via at least one vacuum member of the tissue securing member. Such methods may further involve applying the vacuum force through at least a portion of the vacuum member while not applying the vacuum force through at least another portion of the vacuum member. In some embodiments, applying the compressive force comprises applying force via at least one expansible balloon member. A method may further comprising preventing, using the tissue securing member, a portion of the heart tissue from being treated by the at least one treatment member. For example, the tissue securing member may comprise at least one insulation material for preventing the portion of the heart tissue from being treated.

In some embodiments, visualizing comprises using at least one visualization member selected from the group consisting of an optic imaging device, a thermal imaging device, an ultrasound device, an electrical imaging device and a Doppler imaging device. Some embodiments also include expanding an expansible balloon coupled with the visualization member near an optic element to enhance visualization. Sometimes, expanding the balloon provides a space in a body cavity and/or between at least two body tissues to enhance operation of the optic member. Optionally, expanding the balloon may reduce motion of the heart tissue when applied to the heart tissue.

The invention also includes ablation systems which include an ablation energy source for providing energy to the ablation device. The ablation energy source of the invention is particularly suited for use with ablation apparatus as described herein using RF energy, but is not limited to such use, and other kinds of ablation energy sources and ablation devices may be useable in the invention. A typical RF ablation system comprises a RF generator which feeds current to an ablation device, including those described in this application, containing a conductive electrode for contacting targeted tissue. The electrical circuit is completed by a return path to the RF generator, provided through the patient and a large conductive plate, which is typically in contact with the patient's back.

In some embodiments, the ablation system is configured to recognize the kind of ablation device connected by including keyed plugs, which describes specialized socket shapes configured to accept only plugs which are manufactured with the matching shape. The energy source includes predetermined settings appropriate for the kind of device that is accepted by that socket. In another embodiment, the ablation system of the invention includes apparatus for recognizing the kind of device that has been coupled to the energy source and for automatically adjusting various settings to accommodate the detected device.

In further embodiments the ablation device may be inserted minimally invasively under stress, and is configured to conform to the topography or anatomy of the tissue to be treated when relaxed. This feature may enhance the adherence of the ablation device to the tissue because the suction is not working against resistance of the ablation device to conforming to the desired shape.

In other embodiments, the ablation device may include indicators for identifying which ablation element is to be activated. For example, the ablation device may include different colored lines to assist the user in distinguishing the orientation and alignment of the ablation device.

In some embodiments, the ablation device may be configured to allow the ablation member to extend beyond the edge of the tissue contacting member to allow for ablation to occur outside of the region covered by the tissue contacting member.

In another embodiments, the artery securing arms may instead be configured to grasp a second ablation member, thereby allowing ablation to occur outside of the region covered by the tissue contacting member.

In some embodiments the length of the suction pods may be varied such that suction pods of more than one length are used on the same tissue contact member. Furthermore, the suction pods may be spaced apart or placed in groupings separated by selected lengths. Some or all of the length of the ablation device used to emit ablation energy may not include any suction pods. In some embodiments an insulated member may cover the majority of the geometry of the ablation device such that only areas contacting target tissue can emit energy that will penetrate the tissue. This feature may protect surrounding tissues from unintentional ablation. Positioning the ablation member within an insulating tissue contacting member provides a safety margin protecting adjacent tissue that is not intended to be ablated. The insulated member may include lumens for delivering saline to lower impedance or increase conductivity or other substance to improve performance and efficiency of energy emission.

The suction force may be used to create a fluid gradient through the thickness of the tissue. A dynamic fluid gradient may enhance energy conduction.

In some apparatus and methods of the invention, once the tissue contact member is positioned and suctioned onto the heart, the probe may also be slid within the probe channel in the tissue contact member so that the energy emitting section of the ablation member may be positioned as a separate step from the step of positioning the tissue contacting member. It is also possible to position the tissue contacting member separately from the ablation member, then in a later step, slide the ablation member into the tissue contact member. In some embodiments, an ablation member with a short energy emitting section may be moved along a channel in the tissue contact member so that the device can create long lesions, perhaps longer than the ablation section of the ablation member, with minimal manipulations of the device within the track.

Using a single placement of the tissue contacting member may enhance continuity of ablation lesions. Not having to move the ablation device between discrete ablation cycles, and instead only moving the ablation member within the tissue contacting member, insures that adjacent ablation segments are contiguous with no ablation gaps. Avoiding the creation of gaps can be critical to insure electrical isolation of desired tissue areas, and may also decrease procedure time by not requiring the surgeon to verify overlap of adjacent ablation lesions.

In some embodiments the preferred features of the material used to manufacture the tissue contacting member include one or more of the following: the material provides electrical or thermal insulation, the material is flexible to facilitate remote advancement via tortuous pathways, the material has shape memory allowing large elastic deformation of the tissue contacting member but also allowing the tissue contacting member to return to a preformed shape in a relaxed configuration, the material may be translucent or transparent to help the user see the position of the ablation probe, and the material may be lubricious to facilitate insertion and placement.

The method may further include the steps of using visual and audible cues to verify the ablation device is adhered to tissue. For example the user can hear a suction sound or 'whistle' when the suction has been activated and the ablation device is not correctly adhered. Also, the user can hear vacuum pump elevate as vacuum increases. In some embodiments, the user can visually observe the tissue contacting member collapse when the ablation device is correctly adhered and suction is activated.

In some embodiments, the preferred vacuum pressure is −200 mmHG to −760 mmHG.

In still further embodiments, the ablation device may include more electrodes that are available on the energy source. In this embodiment, the ablation device includes a plurality of electrodes, and wherein the energy source includes fewer electrodes than the ablation device. Further, the ablation device includes at least two plugs, with each plug providing power to a subset of the plurality of electrodes on the ablation device. The method comprises the steps of connecting the first plug of the ablation device to the energy source, applying ablation energy to the tissue, unplugging the first plug from the energy source, plugging the second plug of the ablation device into the energy source, and applying ablation energy to the tissue.

This allows ablation device construction to facilitate longer ablations by utilizing multiple connections to the energy source. For example, if an energy source includes seven electrodes coupled to a single plug to power seven ablation segments on the ablation device, the ablation device could include fourteen or twenty-one separate ablation segments. Each set of seven ablation segments would couple to a separate plug. In use, the first plug is inserted into the energy source and the first set of seven ablation segments is activated. Upon completion of treatment, possibly without moving the ablation device, a second region may be ablated by removing the first plug and inserting the second plug to activate the next seven ablation segments on the ablation device. This embodiment can result in a smaller, less expensive energy source that is still capable of powering a long ablation device.

In yet another aspect, a method for treating heart tissue of a patient to treat a cardiac arrhythmia comprises: advancing at least one treatment member and at least one tissue securing member through an incision on the patient; removably coupling the at least one treatment member with the at least one tissue securing member; visualizing a treatment area in the patient with at least one visualization member; contacting the heart tissue of the patient with the treatment member and the tissue securing member; applying a force, through the tissue securing member, to enhance contact of the treatment member with the heart tissue; and treating the heart tissue, using the at least one treatment member. In some embodiments, and treatment member is advanced through the tissue securing member. Optionally, in some embodiments, the treatment member and the tissue securing member are advanced through a minimally invasive port applied to the patient. Another method of the invention includes the following steps. An introducer is advanced through a first incision into the transverse sinus cavity with obturator fully inserted. At a desired area near the pulmonary veins, the obturator is withdrawn, which allows the introducer to assume its pre-formed J shape reaching around the pulmonary veins, possibly also guided by contact with the pericardium. The introducer is preferably long enough to be inserted through a thoracotomy into the transverse sinus cavity around the pulmonary veins and out through the oblique sinus and out through the same or a different thoracotomy. Another instrument is advanced through the same or different thoracotomy to grasp the distal end of the introducer. The introducer is pulled around the pulmonary veins until the distal end is outside the body of the patient. At this point, both the proximal and distal ends of the introducer are preferably outside the body of the patient. Once the ablation device is in position, suction is applied to adhere the ablation device to the tissue surrounding the pulmonary veins. Ablation energy is applied. Once treatment is complete, the ablation device can be removed.

Various embodiments of the devices and methods described briefly above are further described in the appended drawings and the following detailed description. The description of specific embodiments is provided for exemplary pur-

BRIEF DESCRIPTION OF THE DRAWINGS

FIG. 13 is an assembly drawing of an ablation device in accord with the invention, and an introducer for use with the ablation device.

DETAILED DESCRIPTION OF THE INVENTION

Figure 1:
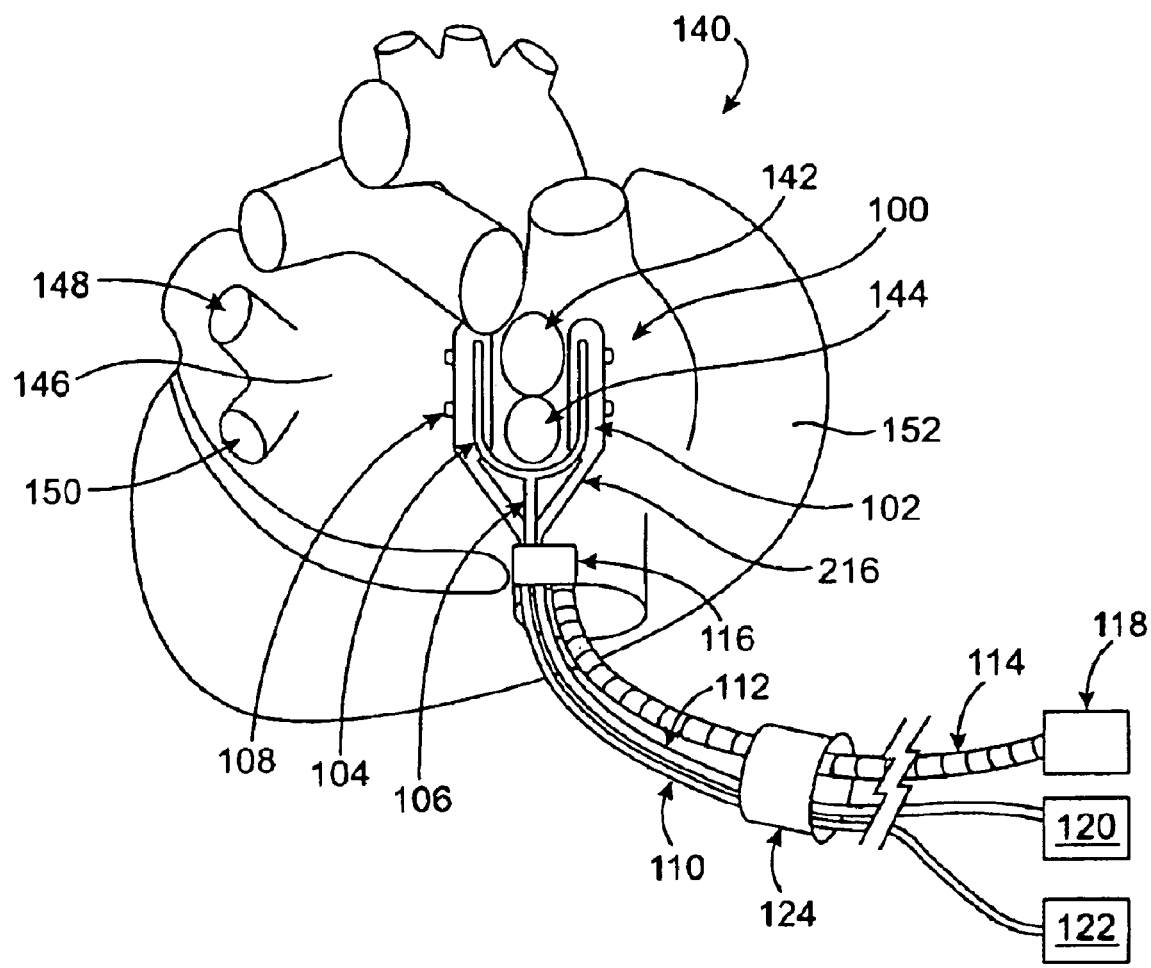
FIG. 1 is a perspective view illustration of a human heart and an ablation device in position for performing an ablation procedure, according to one embodiment of the invention.

The present invention relates generally to medical devices and methods and more specifically to devices and methods for ablating cardiac tissue for treating cardiac arrhythmias such as atrial fibrillation. Ablation of cardiac tissue in various patterns has been shown to disrupt conduction pathways in the heart to ameliorate or eliminate AF or other arrhythmias. The devices and methods will often be used to ablate epicardial tissue in the vicinity of at least one pulmonary vein, but various embodiments may be used to ablate other cardiac tissues in other locations on a heart.

Generally, ablation devices of the invention include at least one tissue contacting member for contacting a portion of the epicardial tissue of a heart, securing means for securing the ablation device to the tissue and at least one ablation member coupled with the contacting member for ablating at least a portion of the tissue. In various embodiments, the devices have features which enable the device to attach to the epicardial surface with sufficient strength to allow the tissue to be stabilized via the device. For example, some embodiments may use suction force to secure the device to epicardial tissue and stabilize a beating heart to enable a beating heart ablation procedure. In some embodiments, the preferred vacuum pressure is −200 mmHG to −760 mmHG. The suction force may be used to create a fluid gradient through the thickness of the tissue. A dynamic fluid gradient may enhance energy conduction. Other embodiments may include other optional features, such as sensors for sensing whether tissue has been ablated, a support member with an arm for connecting the device to a positioning device, cooling apparatus for cooling epicardial tissue, visualization devices and/or the like. Some embodiments of the device are introducible into a patient via minimally invasive means, such as a minimally invasive incision, sheath, trocar or the like. Ablation devices of the invention configured for use in minimally invasive procures will, in some embodiments, be longer than two feet the majority of the probe rests outside of the patient while the active ablation portion of the device is inserted via minimally invasive incision. Some embodiments will further comprise apparatus for reducing kinking of the ablation probe.

In alternate embodiments the length of the suction pods may be varied such that suction pods of more than one length are used on the same tissue contacting member. Furthermore, the suction pods may be spaced apart or placed in groupings separated by lengths of the probe or ablation device. Some or all of the length of the ablation device used to emit ablation energy may not include any suction pods. In such embodiments an insulated member may cover the majority of the geometry of the ablation device such that only areas contacting target tissue can emit energy that will penetrate the tissue. This feature may protect surrounding tissues from unintentional ablation. Positioning the ablation member within an insulating tissue contacting member provides a safety margin protecting adjacent tissue that is not intended to be ablated. The insulated member may include lumens for delivering saline to lower impedance or increase conductivity or other substance to improve performance and efficiency of energy emission. In other embodiments, the ablation device may include indicators for identifying which ablation element is to be activated. For example, the ablation device may include different colored lines to assist the user in distinguishing the orientation and alignment of the ablation device.

The invention also includes ablation systems which include an ablation energy source for providing energy to the ablation device. The ablation energy source of the invention is particularly suited for use with ablation apparatus as described herein using RF energy, but is not limited to such use, and other kinds of ablation energy sources and ablation devices may be useable in the invention. A typical RF ablation system comprises a RF generator which feeds current to an ablation device, including those described in this application, containing a conductive electrode for contacting targeted tissue. The electrical circuit is completed by a return path to the RF generator, provided through the patient and a large conductive plate, which is typically in contact with the patient's back.

In some embodiments, the ablation system is configured to recognize the kind of ablation device connected by including keyed plugs, which describes specialized socket shapes configured to accept only plugs which are manufactured with the matching shape. The energy source includes predetermined settings appropriate for the kind of device that is accepted by that socket.

In another embodiment, the ablation system of the invention includes apparatus for recognizing the kind of device that has been coupled to the energy source and for automatically adjusting various settings to accommodate the detected device.

Methods of the invention generally include contacting a device with epicardial tissue, using a tissue contacting member on the device to secure the device to the tissue, and ablating the tissue with an ablation member on the device. In some embodiments, the method further includes additional steps such as positioning the device on the epicardial tissue, stabilizing cardiac tissue, cooling cardiac tissue, positioning the device using a positioning device, visualizing epicardial tissue with an imaging device and/or the like. Again, although much of the following description focuses on embodiments used to treat AF by ablating epicardial tissue near one or more pulmonary veins on a human heart, the devices and methods may be used in veterinary or research contexts, to treat various heart conditions other than AF, to ablate cardiac tissue other than the epicardium and/or in any other suitable manner or context.

Referring now to FIG. 1, an ablation device 100 is shown in position for ablating epicardial tissue on a human heart 140. A top view of ablation device 100 is shown, the visible components of device 100 including a tissue contacting member 102 coupled with a suction connector 216 and a support member 104 having a support arm 106. Tissue contacting member 102 also includes multiple artery securing arms 108 for securing one or more coronary arteries. Suction connector 216 is coupled with a suction cannula 112, which in turn is coupled with a suction source 120. Support arm 106 is coupled via a clamp 116 to a positioner 114, which in turn is coupled to a stabilizing device 118 for stabilizing positioner 114. Finally, an ablation member (not visible) of ablation device 100 is coupled, via a wire 110, to an energy source 122. In various embodiments, ablation device 100 may be introduced into a patient through a minimally invasive introducer device, such as a sheath 124, trocar or the like, as is represented in FIG. 1 by a simplified representation of sheath 124.

In an alternate embodiment, the artery securing arms 108 may instead be configured to grasp a second ablation member, thereby allowing ablation to occur outside of the region covered by the tissue contacting member. In this embodiment the features 108 are instead auxiliary securing arms. Although example auxiliary securing arms are shown only in FIG. 1, this feature could be used on other ablation device embodiments.

In FIG. 1, ablation device 100 is shown in a position partially encircling the right superior pulmonary vein 142 and the right inferior pulmonary vein 144. As will be described in further detail below, such a position is only one possible configuration for treating heart 140. In other embodiments, for example, both of the right pulmonary veins 142, 144 may be completely encircled, only one may be partially or completely encircled, the left superior 148 and/or left inferior 150 pulmonary veins may be partially or completely encircled and/or various patterns may be ablated on the left atrium 146, the right atrium 152 and/or the right and left ventricles (not labeled). Any ablation pattern suitable for heart treatment may be accomplished by one or more embodiments of the present invention. Thus, the following descriptions of various embodiments should not be interpreted to narrow the scope of the invention as set forth in the claims.

Generally, ablation device 100 includes at least one tissue contacting member 102 coupled with at least one ablation member (not shown in FIG. 1). One embodiment of a device which may be used as tissue contacting member 102 is described in U.S. Patent Application Ser. No. 60/182,048, filed on Feb. 11, 2000, the entire contents of which is hereby incorporated by reference. Ablation device 100 shown in FIG. 1 actually includes two tissue contacting members 102, one on either side of the right pulmonary veins 142, 144. Tissue contacting members 102 may be coupled together via support member 104 and suction connector 216. In other embodiments, some of which will be described below, tissue contacting member 102 may include only one member, more than two members, a coupling member disposed between multiple arms and/or the like. Alternatively, tissue contacting member 102 may be conical, linear, shaped as a flat pad or a flat elongate member or may have any other suitable configuration. Additionally, tissue contacting members 102 may have any suitable size and dimensions. For example, in FIG. 1, tissue contacting members 102 and device 100 in general have a shape and dimensions to contact and ablate epicardial tissue on heart 140 in a pattern partial encircling the right pulmonary veins 142, 144. Many other configurations and sizes are possible, as described further below.

Tissue contacting members 102 may be manufactured from any suitable material, such as a polymer, plastic, ceramic, a combination of materials or the like. In one embodiment, for example, tissue contacting members 102 are manufactured from a liquid molded rubber. In some embodiments, the material used to make tissue contacting members 102 is chosen to allow the members 102 to be at least partially deformable or malleable. Deformable tissue contacting members-102 may allow ablation device 100 to be inserted into a patient and/or advanced to a surgical site within the patient via a minimally invasive incision or a minimally invasive introducer device, such as sheath 124. Deformable tissue contacting members 102 may also allow device 100 to conform to a surface of heart 140, to enhance ablation of epicardial or other cardiac tissue. In some embodiments, tissue contacting members 102 include one or more artery securing arms 108, for securing, exposing and/or occluding one or more coronary arteries via silastic tubing attached between the artery and securing arm 108. Securing arms 108 are generally made of the same material(s) as tissue contacting members 102 but may also suitably comprise other materials.

In some embodiments the ablation device may be inserted minimally invasively under stress, and is configured to conform to the topography or anatomy of the tissue to be treated when relaxed. This feature may enhance the adherence of the ablation device to the tissue because the suction is not working against resistance of the ablation device to conforming to the desired shape.

Thus, some embodiments the preferred features of the material used to manufacture tissue contacting member 102 may further include one or more of the following characteristics: the material provides electrical or thermal insulation, the material is flexible to facilitate remote advancement via tortuous pathways, the material has shape memory allowing large elastic deformation of the tissue contacting member but also allowing the tissue contacting member to return to a pre-formed shape in a relaxed configuration, the material may be translucent or transparent to help the user see the position of the ablation probe, the material may be lubricious to facilitate insertion and placement, and the material allows thin walled construction of the tissue contacting member so that collapse of the tissue contacting member can be seen to confirm the operation of the vacuum when activated.

In some embodiments, tissue contacting members 102 are coupled with support member 104. Support member 104 may be made of any suitable biocompatible material, such as titanium, stainless steel, nickel titanium alloy (Nitinol) or the like. Support member 104 may be coupled with tissue contacting members 102 by any suitable means, such as but not limited to one or more adhesive substances, placement of a portion of support member 104 within a sleeve on tissue contacting members 102 or a combination of both. Like tissue contacting members 102, support member 104 may also be malleable or deformable to allow for insertion of ablation device 100 through a minimally invasive sheath 124 and/or for enhancing conformability of device 100 to a surface of heart 140. Support member 104 typically includes at least one support arm 106 or similar protrusion or multiple protrusions for removably coupling ablation device 100 with positioner 114 or one or more other positioning devices. Positioner 114, for example, may comprise a flexible, positioning arm, with attachment means such as clamp 116 for attaching to support arm 106 and stabilizing device 118 for stabilizing positioner 114. For example, a flexible, articulating positioner 114 may be of the type which rigidities when tensile force is applied, such as via a tensioning wire. Any other suitable positioner 114 may alternatively be used. In other embodiments, device 100 may not include support member 104. Such devices 100 may incorporate a connection arm onto a tissue contacting member 102, may be positioned on heart 140 using a positioning device inserted through a separate incision, or may be positioned or manipulated by a physician or other user via any other suitable means.

Tissue contacting members 102 may also be coupled with one or more suction cannulas 112 to provide suction for enhancing contact of ablation device 100 with epicardial tissue. In various embodiments, tissue contacting members 102 may be directly coupled to one or more cannulas 112 or may be connected via one or more suction connectors 216. In FIG. 1, a V-shaped suction connector is used to couple the two tissue contacting members 102 with a common cannula 112. Cannula 112, in turn, is connected to suction source 120, which may be a conventional wall suction or stand-alone suction source. Generally, cannula 112 may be any suitable conventional cannula 112, which are well known to those skilled in the art. Suction connector 216 is typically comprised of the same material(s) as tissue contacting members 102, but may also be made of a material or materials used to make cannula 112. Suction connector 216 may further include a nozzle 218 (FIG. 2) for connecting to cannula 112.

Figure 2:
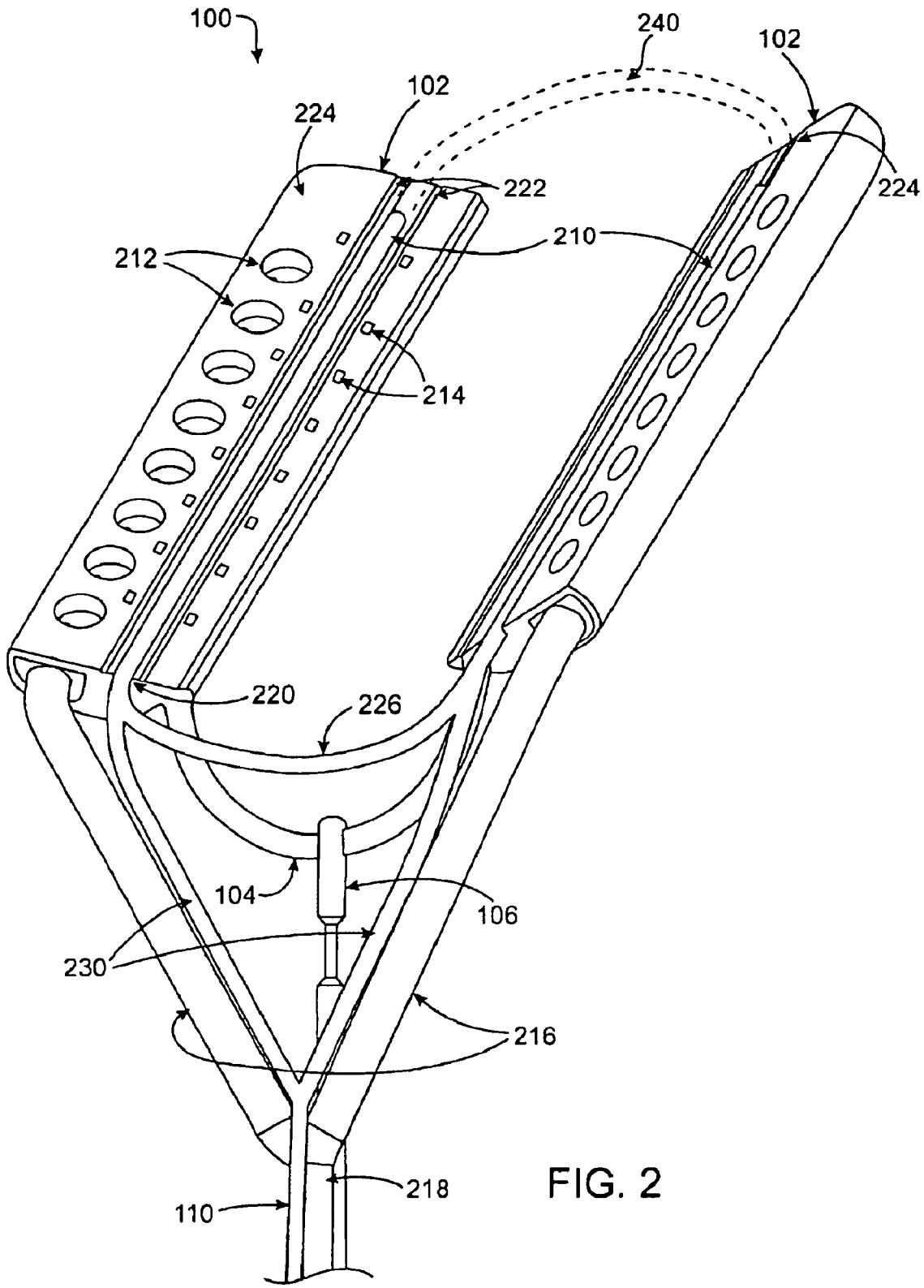
FIG. 2 is a perspective view of an ablation device, according to one embodiment of the invention.

Ablation device 100 also includes at least one ablation member 210 (FIG. 2). Ablation member 210 typically receives energy from a separate energy source 122, although ablation members 210 with internal energy sources are also contemplated. Where a separate energy source 122 is used, ablation member 210 may be coupled with source 122 by any suitable means. In one embodiment, for example, ablation member 210 may be coupled to energy source 122 with wire 110. Wire 110 may be any suitable connector, such as fiber optic cable, electric cable, coaxial cable, ultrasound transmission device or the like. As is described further below, any suitable energy may be provided by energy source 122 for ablation and any means for transmitting energy to ablation member 210 is contemplated within the scope of the invention. In some embodiments, for example, energy may be transmitted remotely, so that no wires or other similar connecting devices are required. In other embodiments, radio frequency energy may be provided by an RF energy source and transmitted to ablation member 210 via conventional electrical wire(s) 110.

Generally, ablation member 210 may be configured to transmit energy of any suitable quantity or force. For example, in some embodiments sufficient energy will be transmitted through ablation member 210 to ablate only epicardial tissue on a heart. In other embodiments, sufficient energy may be transmitted to cause one or more layers beneath the epicardial tissue to be ablated. In some embodiments, for example, one or more transmural lesions (across the entire wall of the heart) may be ablated. Typically, an amount of energy transmitted through ablation member 210 will be adjustable to create a desired ablation depth. In addition, the depth of ablation can also be affected by the contact pressure between the ablation member 210 and the tissue. Generally, the greater the contact pressure between the ablation member 210 and the tissue the deeper the ablation lesion will extend into the tissue. The contact pressure can be adjusted to a desired level by adjusting the mechanical force applied through the tissue contacting members 102 and/or by adjusting the level of suction applied through the suction apertures 212.

In addition, the contact pressure between the ablation member 210 and the tissue gives a degree of directional control over the direction the lesion ablation lesion will extend into the tissue. Only the tissue in contact with the ablation member 210 and in a direction perpendicular to the surface of the tissue will be ablated. Adhering the ablation member 210 to the target tissue with suction applied through the suction apertures 212 assures that only the intended tissue will be ablated and will prevent migration or rollover of the tissue contacting members 102 and ablation member 210.

In this example and other embodiments disclosed herein, the suction apertures 212 may be connected to multiple, separate suction lumens. Optionally, the apparatus may include means for selectively applying vacuum to one or more of the separate lumens without applying vacuum to one or more other separate lumens. Alternatively or in addition, the apparatus may be provided with suction pod plugs that serve to occlude one or more of the suction apertures 212 so that suction is applied only through the remaining suction apertures 212 that have not been occluded with a suction pod plug.

As mentioned briefly above, a minimally invasive introducer sheath 124, trocar or other minimally invasive device may be used for introducing one or more of the components shown in FIG. 1 into a patient. In some embodiments, a sheath need not be used and instead only a minimally invasive incision is used. In other embodiments, multiple minimally invasive incisions and/or sheaths 124 may be used for introducing various devices into a patient. For example, one sheath 124 may be used for introducing ablation device 100 and another sheath 124 may be used for introducing positioner 114. Although devices and methods of the present invention are often suitable for minimally invasive procedures, they may also typically be used in open surgical procedures, either with or without cardiopulmonary bypass, in various embodiments.

Referring now to FIG. 2, an embodiment of ablation device 100 is shown in further detail. Device 100 is shown from a bottom/angled view to show a tissue contacting surfaces 224 of tissue contacting members 102, ablation member 210, suction apertures 212 and sensors 214. Like tissue contacting members 102, tissue contacting surfaces 224 may be given any configuration and sizes to contact cardiac tissue in an area around the tissue to be ablated. For example, in an embodiment as in FIG. 2 a tissue contacting surface 224 on one tissue contacting member 102 may have a length of approximately 1.25 in. and a width of approximately 0.5 in., with a space between the two tissue contacting surfaces measuring approximately 0.4 in. Such exemplary dimensions are in no way limiting, and all combinations of dimensions for one or more tissue contacting members 102 are contemplated. In some embodiments, as in FIG. 2, surfaces 224 may be flat and smooth. In other embodiments, surfaces 224 are textured, curvilinear or otherwise shaped to enhance contact of tissue contacting members 102 with heart 140. Some embodiments may further include one or more surface features 222. Such features 222 may enhance friction between tissue contacting surfaces 224 and epicardial tissue and/or may provide an area for placement of additional features, such as irrigation apertures for cooling tissue or the like.

Ablation member 210 may include one or more ablation members for transmitting one or more of a variety of ablation agents to epicardium or other cardiac tissue. In some embodiments, as commonly shown in the drawing figures, ablation member 210 may comprise a single, continuous, RF ablation coil or wire for transmitting RF energy to cardiac tissue. In other embodiments, ablation member 210 may be multiple radio frequency devices or one or more cryogenic devices, ultrasound devices, laser devices, thermo-electric chip devices, chemical agent delivery devices, biological agent delivery devices, light-activated agent devices, thermal devices, microwave devices, or ablating drug delivery devices. Other suitable ablation devices are also contemplated within the scope of the invention. Additionally, radio frequency ablation members 210 may be bipolar or unipolar in various embodiments. In conjunction with any of these various embodiments, energy source 122 may provide any of the above-listed types of ablative energy or substance, any combination thereof or any other suitable ablative energy or substance.

Ablation member 210 may be given any configuration or size for ablating cardiac tissue. In the embodiment shown in FIG. 2, for example, ablation member 210 has two linear portions disposed along most of the lengths of contacting surfaces 224 of tissue contacting members 102, and the linear portions are continuous with a curved portion 226 so that ablation member 210 is generally U-shaped. Alternatively or additionally, ablation member 210 may continue proximally from tissue contacting members 102 in one or more arms 230 which eventually connect to wire 110 or other connective device. In some embodiments, curved portion 226 may be eliminated so that ablation member 210 comprises two linear ablation members connected to wire 110 via arms 230. In yet other embodiments, arms 230 may be eliminated and ablation member 210 may be coupled directly to wire 110 without interposing arms.

Generally, ablation members 210 and tissue contacting member 102 may have any shapes, sizes, configurations or combinations of shapes and sizes to produce a desired ablation pattern on epicardial or other tissue of a heart. In some examples, ablation members 210 and tissue contacting members 102 are configured to partially or completely encircle or surround one pulmonary vein. In other embodiments, they may be configured to partially or completely surround two pulmonary veins on the same side of the heart, such as the left superior and left inferior pulmonary veins. In still other embodiments, the right and left inferior pulmonary veins or the right and left superior pulmonary veins may be partially or wholly encircled. And in still other embodiments, all four pulmonary veins may be partially or completely encircled by ablation members 210 and tissue contacting member 102. Some of these embodiments are described in further detail below, but it should be understood that any possible configuration is contemplated within the scope of the present invention.

In some embodiments, all or a portion of ablation member 210 or tissue contacting member 102 may be steerable. Steerability means that an ablation member 210 or tissue contacting member 102 may be adjusted to fit around or next to one or more pulmonary veins or to otherwise assume a desired configuration. For example, some embodiments may include a pull wire coupled with ablation member 210 and/or tissue contacting member 102. The pull wire, when pulled, deflects ablation member 210 and/or tissue contacting member 102 to one side or around a curved structure. Other embodiments may include pushable wires, combinations of flexible and stiff portion and/or the like to provide steerability.

In some embodiments, for example, it is desirable to ablate epicardial tissue in a circumferential pattern around one or more pulmonary arteries. Various configurations of tissue contacting members 102 and ablation members 210 are contemplated for achieving such ablation patterns. For example, a retractable RF coil 240 or other retractable ablation device may be incorporated into or used in conjunction with ablation member 210 as shown in FIG. 2. Retractable coil 240 could be housed within tissue contacting member 102, for example, and could be released when desired to surround or encircled one or two pulmonary veins. As already described, the RF ablation member 210 and/or the RF retractable coil 240 pictured in FIG. 2 may be replaced, in other embodiments, with devices using radio frequency energy, ultrasound energy, microwave energy, cryogenic energy, thermoelectric energy or laser energy for ablating tissue. For example, ablation member 210 in some embodiments comprises multiple thermoelectric chips disposed in a pattern on tissue contacting members 102.

Although ablation device 100 and ablation member 210 are often shown as being generally U-shaped, many other configurations are possible. As described further below, a ablation device 100 may be conical in shape, with ablation member 210 being disposed in a circle at the base of the cone which contacts cardiac tissue. In other embodiments, device 100 may be configured as a flat patch and one or more linear or curvilinear ablation members 210 may be incorporated into the patch. For example, ablation device 100 may include a combination of multiple ablation members 210 to ablate a pattern on heart 140 such as: a first linear ablation member for contacting heart tissue between a left pulmonary vein and a right pulmonary vein; a second linear ablation member for contacting heart tissue at a location approximating a line extending to the atrioventricular groove; and a third linear ablation member for contacting heart tissue on a left atrial appendage. In such an embodiments, one or more of ablation members 210 may overlap one another. In some embodiments involving multiple ablation members 210, each member may be controllable on a separate radio frequency channel or other energy transmission channel.

Tissue contacting members 102 optionally include one or more attachment means for enhancing contact of ablation device 100 with epicardial or other cardiac tissue. In some embodiments, one or more suction apertures 212 are used. Each suction aperture 212 generally includes a depressed surface and a small suction hole. The suction hole is connected to a lumen (not shown) within tissue contacting member 102, and the lumen is then couplable with a suction cannula 122 or connector 216 for connecting to cannula 122. Suction apertures 212 may be given any suitable configuration, size or pattern. For example, suction holes may be disposed on tissue contacting member 102 is a largely linear pattern, as in FIG. 2. In other embodiments, suction apertures may be arranged in two parallel lines such that ablation member 210 is disposed between the two parallel lines of suction apertures 212. In still another embodiment, ablation device 100 may include one tissue contacting member 102 having a conical shape, with the base of the cone contacting epicardial tissue and the entire conical tissue contacting member 102 acting as one suction aperture.

In some embodiments, suction force may be applied via suction apertures 210 with sufficient strength to allow for stabilization and/or positioning of heart 140. For example, a physician may place ablation device 100 on a beating heart 140, apply suction, and hold heart 140 is a relatively stable or reduced-motion position while performing an ablation procedure. The physician may also (or alternatively) turn or otherwise move heart 140, using ablation device 100, such as when a different angle of heart 140 would be advantageous for viewing or treating a portion of heart 140. In these or other embodiments, suction force applied through suction apertures 212 may be of sufficient strength to dissect through one or more layers of adipose tissue covering epicardial tissue. Such dissection by suction apertures 212 may allow for improved contact of the epicardial tissue by device and, thus, improved ablation. In alternative embodiments, suction apertures 212 may be replaced or supplemented by other means for securing ablation device 100 to epicardial tissue. For example, an adhesive may be applied to tissue contacting surfaces 224. Such adhesives or other securing means may also be sufficiently strong, in some embodiments, to allow for positioning and/or stabilization of heart 140.

Referring to FIG. 2, tissue contacting members 102 may also include one or more sensors 214 for judging the thickness of the tissue or to determine the amount of therapy or energy that must be delivered to the tissue, for sensing whether the ablation device 100 is properly positioned in contact with the tissue to be ablated, and to monitor the progress of the ablation to recognize when the tissue along a selected length of the ablation device 100 has received sufficient treatment and communicates with a means for directing the ablation device 100 to discontinue or reduce treatment at that site; in some embodiments, while continuing to apply ablation energy at other locations along the length of the ablation device 100. For these and other purposes, the sensors 214 may include one or more thermal sensors, electrical sensors, thermoelectric sensors, microchips, thermistors, thermocouples, Doppler sensors, microwave sensors, and ultrasonic sensors.

As shown in FIG. 2, some embodiments include two or more paired sensors 214, with one sensor of each pair on one side of ablation member 210 and the other sensor on the opposite side. In some embodiments, one sensor 214 transmits a signal through epicardial tissue to its paired sensor 214. If epicardial tissue between the two paired sensors 214 has been ablated, then energy will transmit poorly through that ablated tissue. Thus, the receiving sensor 214 will receive reduced or no energy transmitted from the transmitting sensor 214. If tissue between two paired sensors has not been ablated, the signal should travel through the tissue with only slight reduction in strength. By using such paired sensors 214 and comparing signals received in different pairs, areas of ablation can be compared, to determine if all desired areas for ablation have been sufficiently ablated. Other configurations one or more sensors 214 may also be used.

Figure 2A:
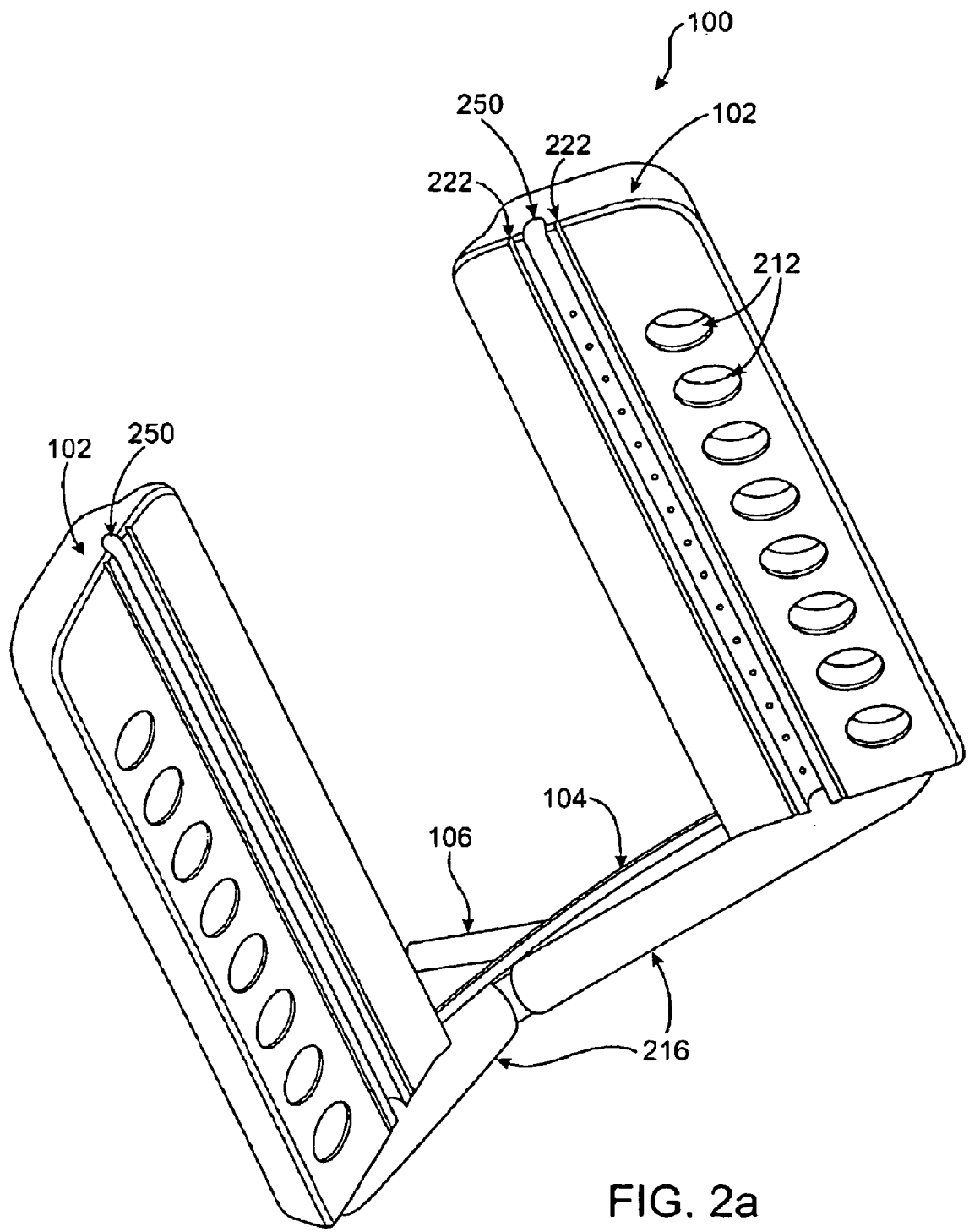
FIG. 2a is a perspective view of the ablation device shown in FIG. 2, with the ablation member removed.

Referring now to FIG. 2a, another view of ablation device 100 as in FIG. 2 is shown, with ablation member 210 removed for clarity. In some embodiments, tissue contacting members 102 include a linear trough 250 in which ablation member 210 is placed, either removably or permanently. Positioning ablation member 210 in trough 250 may provide improved contact between ablation member 210 and epicardial tissue while also providing ablation device 100 with durability. Surface features 222 are again shown in FIG. 2a. These features may simply enhance contact of tissue contacting members 102 with epicardial tissue or may also contain additional features, such as sensors, irrigation apertures for allowing passage of irrigation fluid for cooling ablated tissue, small suction apertures and/or the like.

Optionally, various embodiments of ablation device 100 may further include at least one cooling member for cooling a portion of ablated epicardial tissue, epicardial tissue surrounding an ablated area, other nearby tissues and/or a portion of device 100. Cooling members are not shown in the drawing figures, for purposes of clarity. Generally, a cooling member may comprise any suitable device for cooling a tissue. In some embodiments, cooling member includes at least one inlet port, for allowing introduction of a cooling substance into the member, a hollow internal cooling member, and at least one outlet port for allowing egress of the cooling substance. The cooling substance itself may be carbon dioxide, any other suitable gas, saline or any other suitable liquid. In some embodiments, the hollow cooling member comprises a tubular member disposed within tissue contacting member 102 in general proximity with ablation member 210. In other embodiments, cooling member may comprise a chamber for containing cooling substance or a series of irrigation holes for allowing cooling substance to flow out of tissue contacting member 102 to contact ablated or other epicardial tissue. Many other suitable cooling apparatus are contemplated for use within the scope of the present invention.

Figure 3:
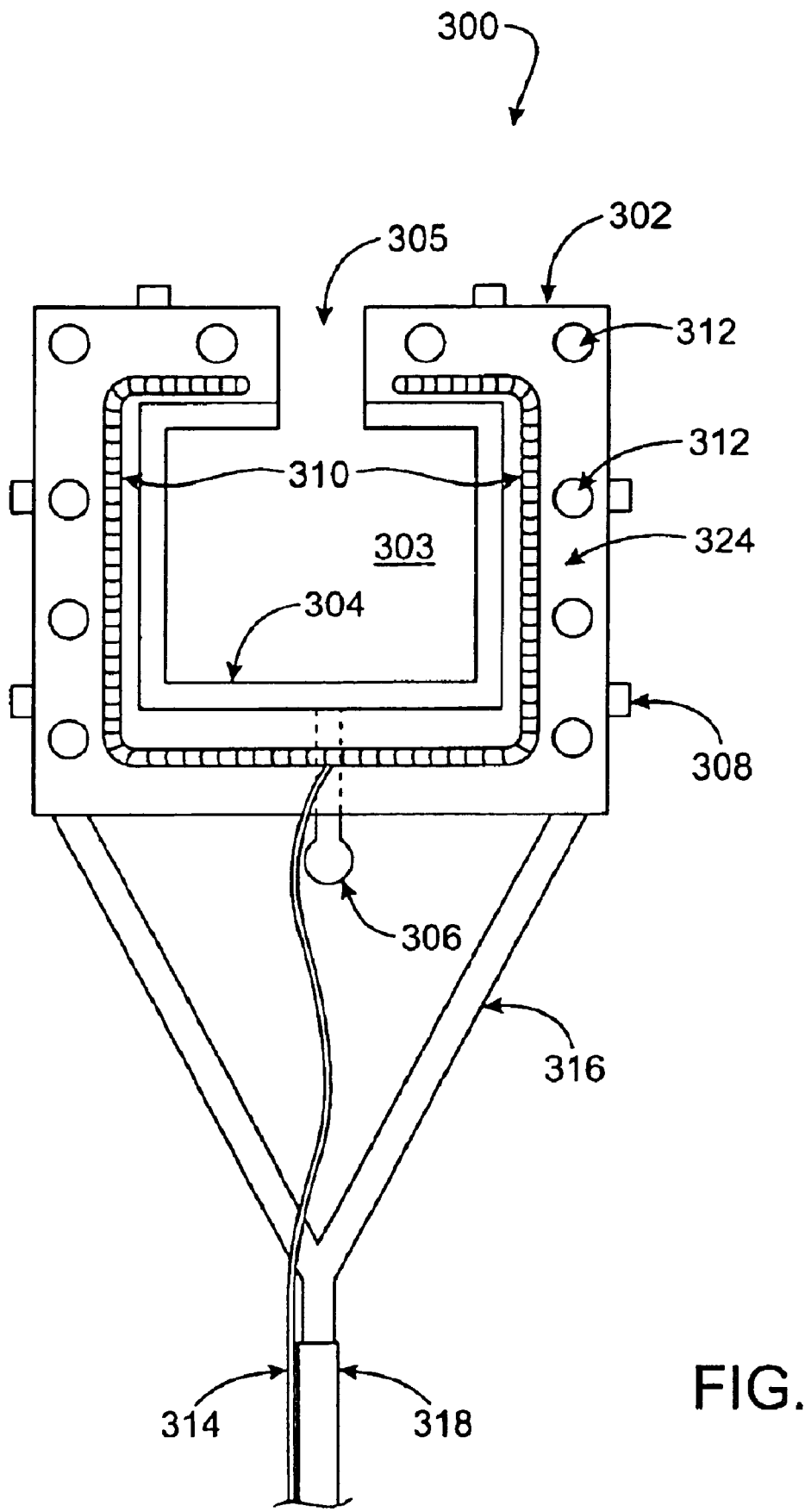
FIG. 3 is a bottom-surface view of an ablation device, according to one embodiment of the invention.

With reference now to FIG. 3, another embodiment of ablation device 300 is shown from a bottom-side view. Ablation device 300 includes a tissue contacting member 302, coupled with an ablation member 310 and a support member 304. As with some above-described embodiments, tissue contacting member includes a tissue contacting surface 324, tissue attaching means including multiple suction apertures 312 and multiple artery securing arms 308. Tissue contacting member 302 is removably couplable with a suction cannula 318 via a V-shaped suction connector 316. Ablation member 310 is coupled with energy transmitting wire 314 for coupling with an energy source (not shown). Support member 304 includes a support arm 306 (shown partially in dotted lines, since it extends on the opposite side of tissue contacting member 302) for coupling device 300 with a positioning device.

In ablation device 300, tissue contacting member 302, ablation member 310 and support member 304 are all generally shaped as a square with a central area 303 and a top area 305 left open. Such a configuration may be used, for example, to contact and ablate epicardial tissue almost completely encircling one or more pulmonary veins. Leaving top area 305 open may allow device 300 to be positioned around such veins or other vessels while still providing almost circumferential ablation. In other embodiments, either central area 303, top area 305 or both may be closed to provide for different contact and/or ablation patterns on epicardial tissue. In still other embodiments, one or more hinges may be positioned on ablation device 300 to allow top area 305 to be closed after positioning device 300 around one or two pulmonary veins. Again, any configuration, shape, size, dimensions or the like are contemplated within the scope of the invention.

Figure 4:
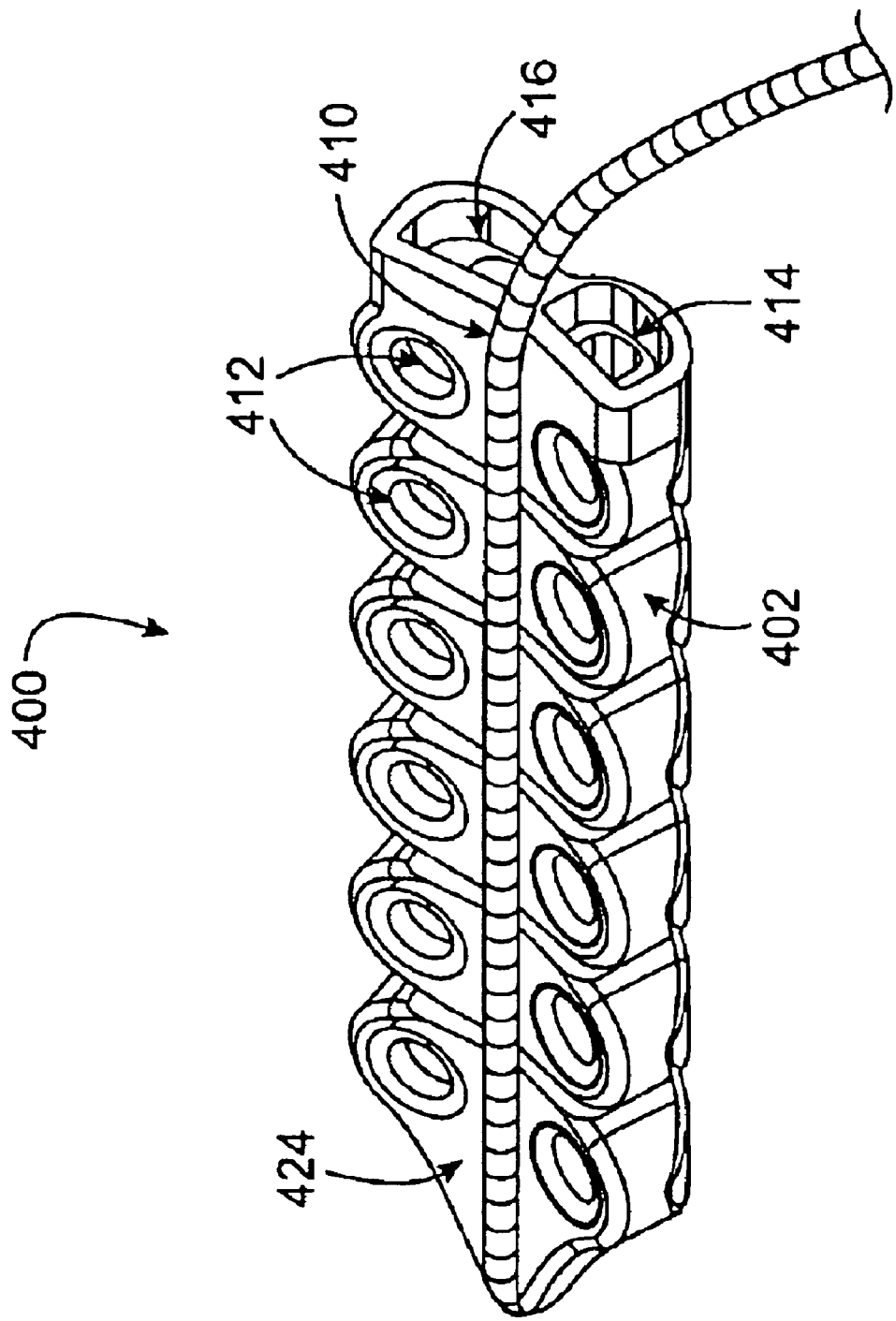
FIG. 4 is a perspective view of a flexible, elongate ablation device with two rows of suction apertures, according to one embodiment of the invention.

Referring now to FIG. 4, another embodiment of ablation device 400 comprises a largely flexible device which includes a tissue contacting member 402 and an ablation member 410. Tissue contacting member 402 may be made of any suitable, flexible material, such as a silicone, polyurethane, polycarbonate, another suitable polymer or combination of polymers or the like. Tissue contacting member 402 generally includes a tissue contacting surface 424 having multiple suction apertures 412. Tissue contacting surface 424 may be slightly concave (as shown), flat or may have any other suitable shape. Suction apertures 412 are disposed in two parallel lines, one line on either side of ablation member 410 and communicate with suction lumens 414 and 416. Suction lumens 414, 416 may be coupled with one or more suction cannulas or similar devices for providing suction force through suction apertures 412. Other embodiments may include one common suction lumen for connection to a suction cannula.

As with various embodiments described above, any suitable ablation means may be used as ablation member 410 in device 400. In the embodiment shown, ablation member 410 comprises a linear radio frequency coil. Ablation member 410 may extend beyond the length of tissue contacting member 402, either in a proximal or distal direction and may be coupled with a source of energy via a wire (not shown) or other connection device. In various embodiments, one or more of the features described above, such as support members, retractable ablation elements, sensors, cooling members, positioning arms and/or the like may be incorporated into or used with ablation device 400. Alternatively, ablation device 400 may simply include tissue contacting member 402 and linear ablation member 410. Such an embodiment may be advantageous for introduction through a narrow, minimally invasive introducer sheath, due to the device's flexibility and relatively small size. In one embodiment, for example, device 400 may measure approximately 3.25 in. in length and approximately 0.9 in. wide and may further be deformable to a narrower configuration for insertion through a sheath. Furthermore, device 400 may be sufficiently flexible to conform to curved surfaces of heart 140, allowing for enhanced contact with and ablation of epicardial tissue. Finally, it may sometimes be advantageous to ablate epicardial tissue in a linear pattern or in multiple line. Ablation device 400 may be movable, to allow ablation in a first line, a second line, a third line and/or the like.

Figure 4A:
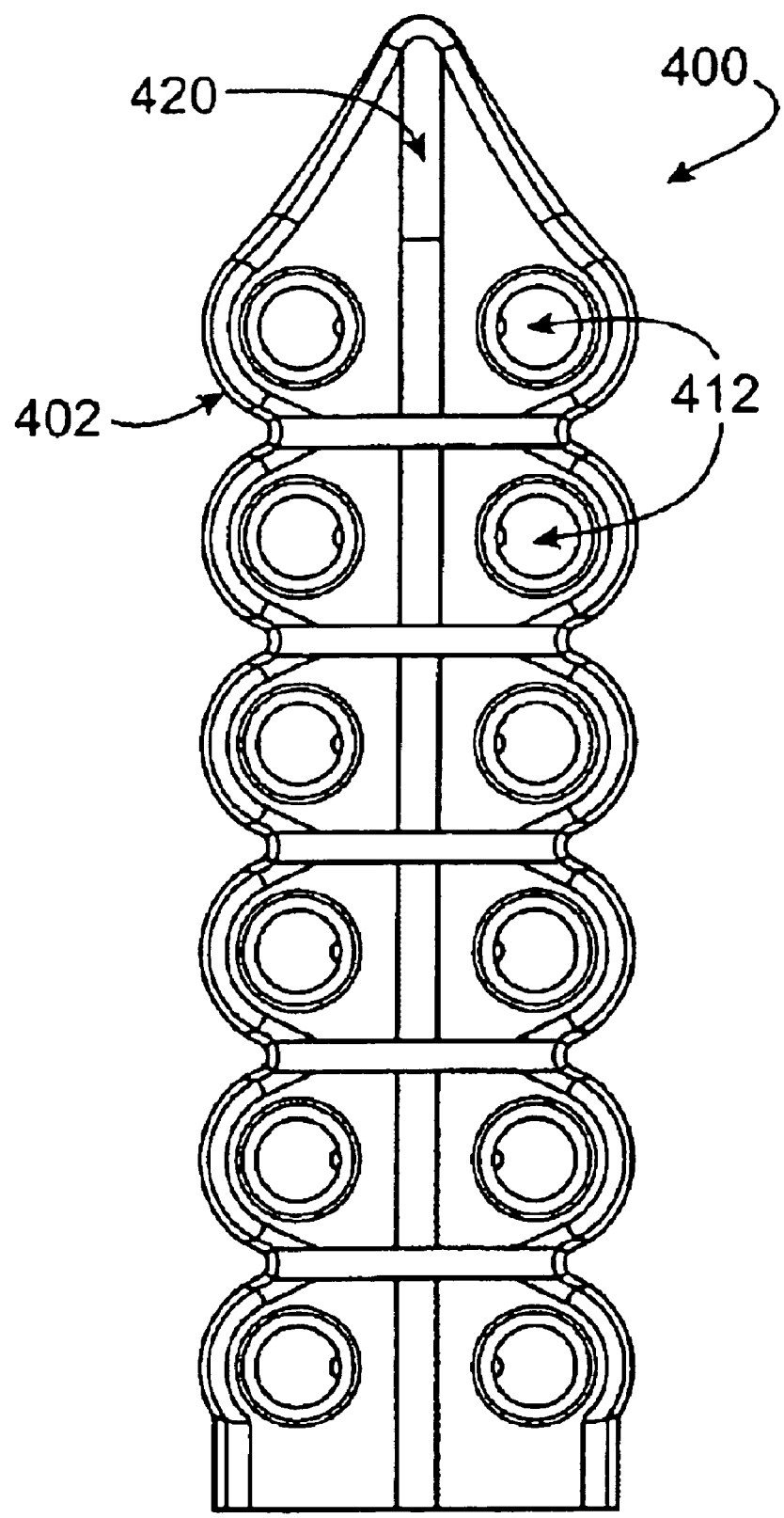
FIG. 4a is a bottom-surface view of the ablation device as shown in FIG. 4, with the ablation member removed.

Referring now to FIG. 4a, a bottom-side view of ablation device 400 is shown with ablation member removed. It can be seen that tissue contacting member 402 may include a trough 420 in which ablation member 410 may be positioned. In some embodiments, ablation member 410 may be a removable piece which may be removably attached to tissue contacting member 402, at least partially disposed within trough 420, so that one ablation member 410 may be used with multiple tissue contacting members 402, one after another, for example if tissue contacting members 402 are single-use, disposable devices.

In some apparatus and methods of the invention, once the tissue contact member is positioned and suctioned on to the heart, the ablation device 400 may also be slid within the trough 420 in the tissue contact member 402 so that the energy emitting section of the ablation member 410 may be positioned as a separate step from the step of positioning the tissue contacting member 402. It is also possible to position the tissue contacting member 402 separately from the ablation member 410, then in a later step, slide the ablation member 410 into the tissue contact member 401. In some embodiments, an ablation member 410 with a short energy emitting section may be moved along a trough 420 in the tissue contact member 401 so that the ablation device 400 can create long lesions, perhaps longer than the ablation section of the ablation member 410, with minimal manipulations of the device within the track.

Using a single placement of the tissue contacting member may enhance continuity of ablation lesions. Not having to move the ablation device between discrete ablation cycles, and instead only moving the ablation member within the tissue contacting member, insures that adjacent ablation segments are contiguous with no ablation gaps. Avoiding the creation of gaps can be critical to insure electrical isolation of desired tissue areas, and may also decrease procedure time by not requiring the surgeon to verify overlap of adjacent ablation lesions.

Figure 5:
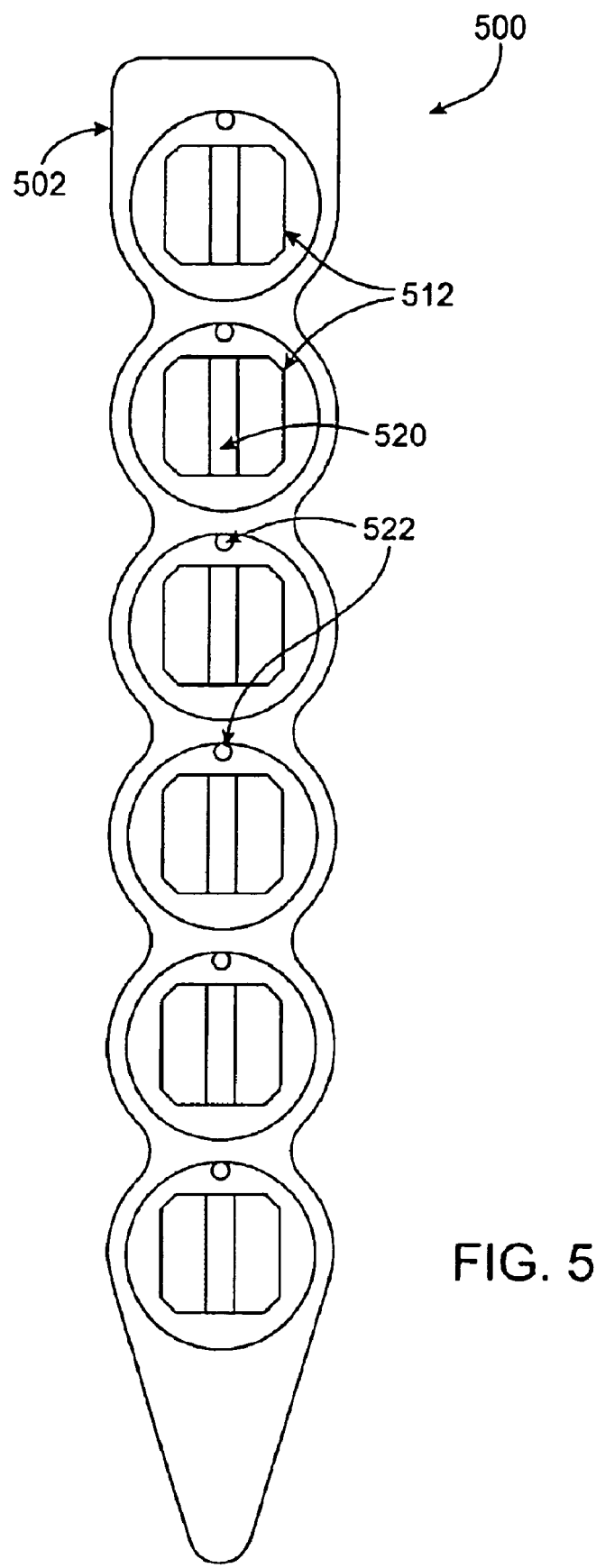
FIG. 5 is a bottom-side view of a flexible, elongate ablation device with one row of suction apertures, according to one embodiment of the invention.

FIG. 5 shows yet another embodiment of ablation device 500, including a tissue contacting member without an ablation member being shown. Device 500 is similar to ablation device 400, but tissue contacting member 502 has one row of suction apertures 512 rather than two and ablation member, placed in ablation trough 520, overlays suction apertures 512. Suction holes 522 shown in suction apertures 512 demonstrate that the apertures sometimes include both a depressed or concave surface and one or more holes communicating with a suction lumen. The embodiment of ablation device 500 in FIG. 5 may be advantageous for forming one or more linear ablations on heart 140 when there is minimal space in which to manipulate device 500 and/or when a narrow, minimally invasive incision or sheath is desired for insertion of device 500. Device 500 may be manufactured from any suitable material or combination of materials, such as those described above, may use any suitable form of ablation member and may include various additional features as desired.

Figure 5A:
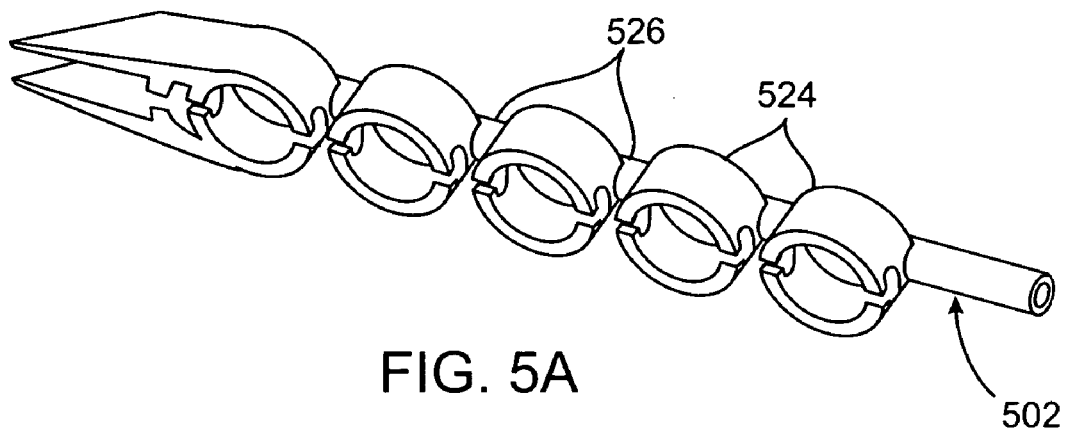
FIGS. 5a, 5b, and 5e are perspective views of another embodiment of a flexible, elongate ablation device with one row of suction apertures, separated by flexible joining members.
Figure 5B:
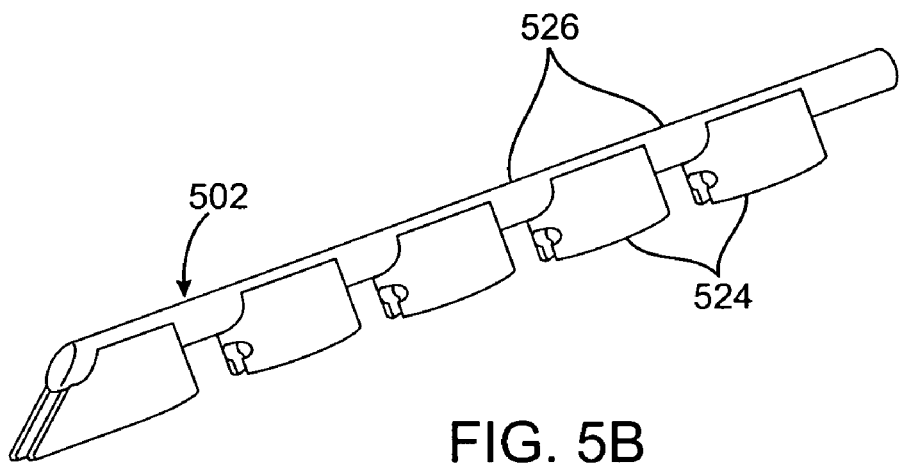
Figure 5C:
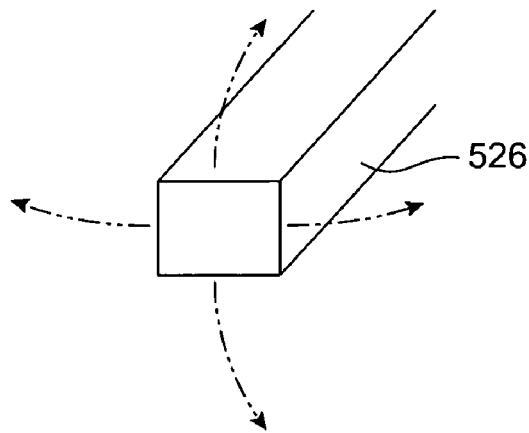
FIGS. 5c and 5d show several alternate cross sections of the flexible joining members of FIGS. 5a and 5b.
Figure 5D:
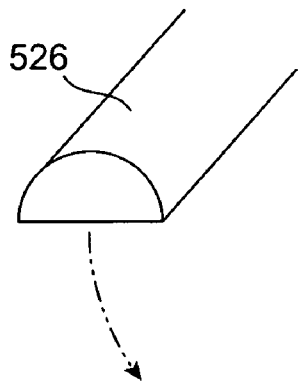
Figure 5E:
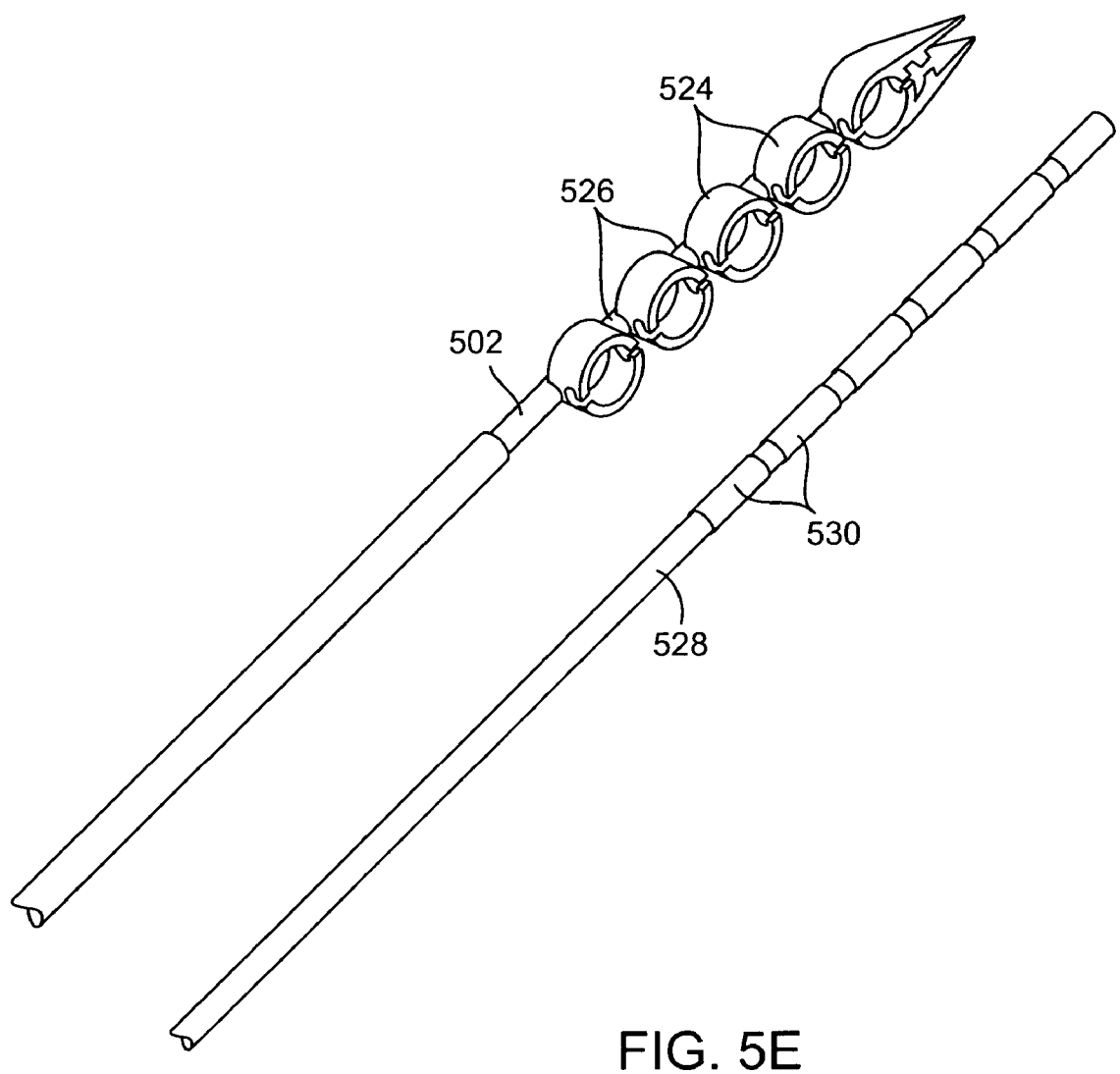

FIG. 5a is a bottom perspective view of an alternate another embodiment suction pods 524 spaced some distance apart and joined by a flexible joining members 526, which may also be used to provide a channel for a vacuum lumen. The distance between the suction pods 524 and the flexibility of the joining members 526 between the suction pods 524 has been found to increase the ability of the tissue contacting member 502 to bend in sharp turns. In FIGS. 5a and 5b, the joining members 526 are cylindrical in cross section, which may improve the overall flexibility of the ablation device 500 in all directions. The flexibility can be varied as desired by changing the thickness, shape, and size of the joining members 526 between the suction pods 524, and by varying the flexibility of the material used to fabricate the joining members 526. For example, FIGS. 5c and 5d show example alternate joining member 526 cross sections. The square cross section of FIG. 5c may allow bending in X and Y axes, but may resist axial rotation. The example cross section shown in FIG. 5d may allow bending in a downward vertical direction, but may resist bending in lateral directions. FIG. 5E shows an ablation member 528 including ablation segments 530 configured for insertion of tissue contacting member 502.

Figure 6:
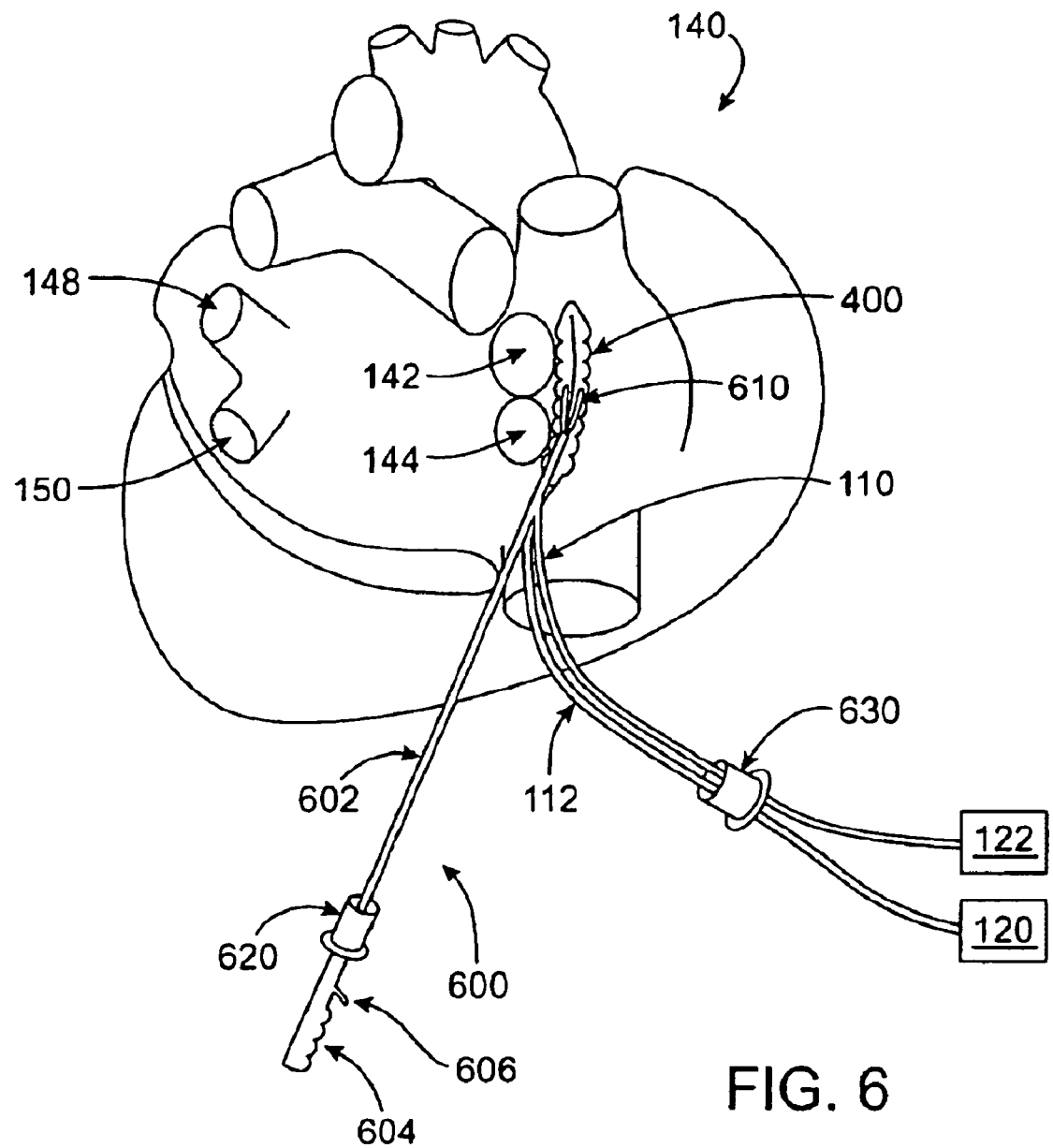
FIG. 6 is a perspective view of a human heart and an ablation device in position for performing an ablation procedure, according to one embodiment of the invention.

Referring now to FIG. 6, ablation device as described with reference to FIGS. 4 and 4a is shown in position for performing epicardial ablation on a human heart 140. Generally, ablation device 400 may be placed in any desired position on heart 140 for ablating epicardial tissue. Thus, in various embodiments device may be placed adjacent one or both of the right pulmonary veins 142, 144, adjacent one or both of the left pulmonary veins 148, 150, or in any other suitable location. Furthermore, ablation device 400 may be used to ablate tissue in a linear pattern at one location and then may be moved to ablated tissue in a linear pattern in another location. As discussed above with reference to various embodiments, ablation device 400 may be introduced into a patient via a minimally invasive device, such as a sheath 630 or trocar, and may be coupled with a source of suction 120 via a suction cannula 112 and with a source of ablative energy 122 via a wire 110 or other connective device.

Ablative device 400, as well as other embodiments of ablative devices described above, may be positioned on heart 140 via a positioning device 602 which is introduced via a second minimally invasive incision or second sheath 620. Second sheath 620 may be placed at any suitable location on the patient to allow access to ablation device with the positioning device 602. Positioning device 602 may then be introduced through sheath and advanced to the position of ablation device 400. Positioning device 602 may then be used to secure device 400, such as by opposable jaws 610 or any other suitable means, and position device 400 in a desired location on heart 140. In some embodiments, positioning device may further be used to reposition device 400 to perform ablation in multiple locations on heart 140. The proximal end of positioning device 602 may include a handle 604 for holding and manipulating device 602 and one or more actuators 606, such as a trigger for opening and closing opposable jaws 610 or other distally positioned end effectors of device 602. Examples of positioning device 602 may include, but are not limited to, conventional minimally invasive surgical devices such as laproscopic surgical devices and the like.

Figure 7:
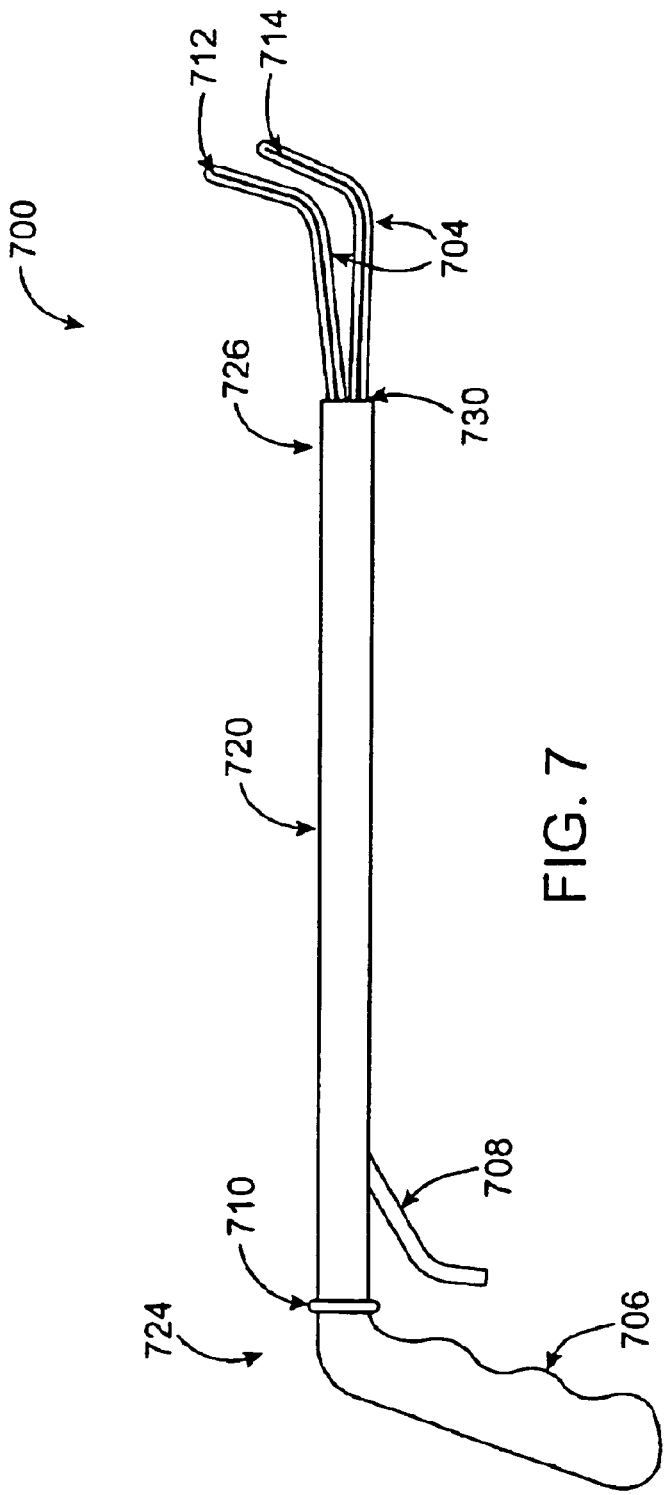
FIG. 7 is a perspective view of an elongate shaft ablation device, according to one embodiment of the invention.

Referring now to FIG. 7, another embodiment of ablation device 700 suitably includes at least one elongate shaft 702 having a proximal end 724 and a distal end 726, a jaw member 704 coupled with shaft 702 near distal end 726, at least one ablation member 712, 714 coupled with jaw member 704, and a handle 706 and at least one actuator 708, 710 near the proximal end 724 for manipulating device 700, opening and closing the jaw member, activating ablation member 712, 714 and the like. Device 700 is generally configured to be introduced through a minimally invasive sheath, trocar or incision, though it may also be used in open surgical procedures. Shaft 702 may be made of any suitable material, such as metal, ceramic, polymers or any combination thereof, and may be rigid along its entire length or rigid in parts and flexible in one or more parts. In various embodiments, the shaft may be malleable, may articulate about at least one joint and/or may be steerable for positioning the device. In some embodiments, the ablation member is coupled with a portion of the shaft.

Jaw member 704 may be disposed on or near distal end 726 of shaft 702 and is generally configured to open and close to grasp epicardial or other tissue between the opposing jaws. For example, jaw member 704 may be coupled with shaft 702 at a hinge point 730 to allow for such opening and closing motion. An ablation member is coupled with at least part of jaw member 704. As with the above-described embodiments, the ablation member may use any suitable energy source for ablating tissue. In some embodiments, multiple ablation members 712, 714 may be used. For example, one electrode 712 of a bipolar ablation member may be coupled with one opposing jaw and another electrode 714 may be coupled with the other opposing jaw. Alternatively, ablation members 712, 714 may include one unipolar ablation device or any of the ablation devices described with reference to various embodiments above. The jaw member and/or the ablation member may be shaped to contact and ablate the epicardial tissue in a pattern such as, but not limited to, a U-shaped pattern, an L-shaped pattern, a circular pattern or a linear pattern. Actuators 708, 710 may have one or more various functions, such as opening and closing jaw member 704, activating ablation members 712, 714, changing an angle of orientation of jaw member 704, straightening or bending jaw member 704 and/or the like. One actuator 710, for example, may comprise a trigger-like actuator while another actuator 708 may comprise a turnable dial.

Generally, jaw member 704 may have any suitable configuration for contacting a surface of a heart, for grasping epicardial or other tissue to be ablated and/or for placing ablation members 712, 714 in contact with tissue to be ablated. As such, jaw members 714 may be straight, curved, bent or otherwise configured for contacting, grasping and/or ablating tissue.

Figure 7A:
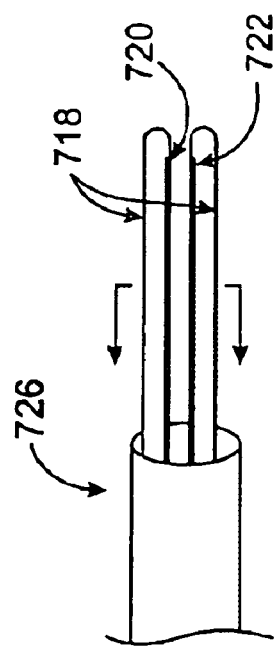
FIG. 7a is a perspective view of the distal end of a shaft as in FIG. 6, with straight jaws, according to one embodiment of the invention.

In some embodiments, jaw member 704 may be adjustable via an actuator 708, 710, so as to allow their shapes to be bent, straightened or the like during a procedure. With reference to FIG. 7a, one embodiment of a straight jaw member 718 may allow jaw member 718 to be retracted within shaft (arrows). Retraction may help protect a patient as well as jaw member during insertion and advancement of the device within the patient. Again, ablation members 720, 722 on such straight jaw members 718 may be bipolar RF members, unipolar RF members or any other suitable ablation devices.

Optionally, the device may further include an insulation member at least partially surrounding the device to protect body structures in the vicinity of the epicardial tissue to be ablated from damage due to heat or electrical current. Also optionally, the ablation member may be adjustable to deliver two or more varying amounts of ablative energy to two or more locations on the epicardial tissue. Various embodiments may further include at least one sensor for sensing a quantity of ablation provided by the ablation member to the tissue.

Figure 8:
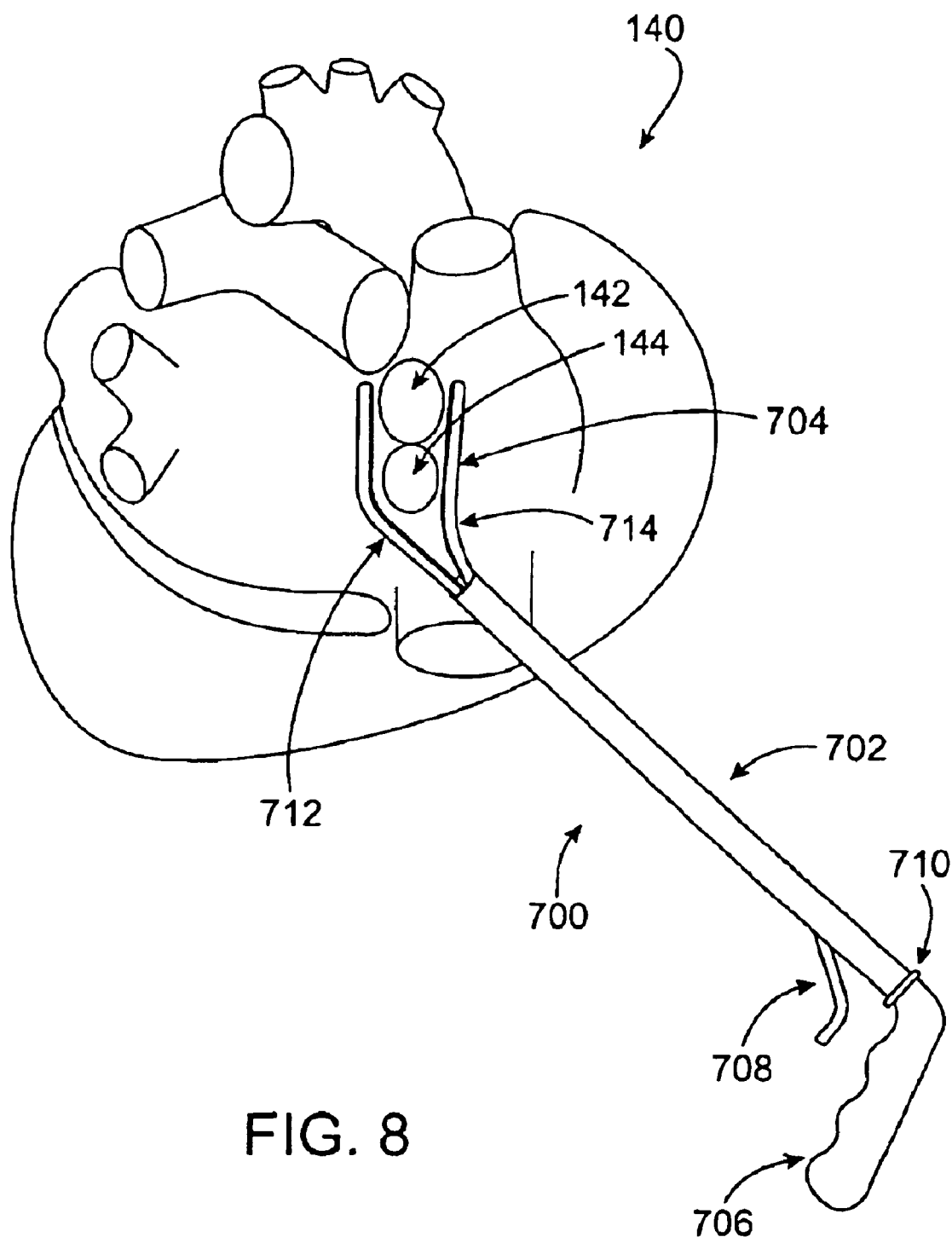
FIG. 8 is a perspective view of a human heart and an elongate shaft ablation device in position for ablating cardiac tissue, according to one embodiment of the invention.

FIG. 8 shows ablation device 700, as just described, in a position for performing an ablation procedure on epicardial tissue of heart 140. Device as shown will ablate in a pattern approximating two lines adjacent the right pulmonary veins 142, 144. It should be understood, from the foregoing descriptions of various embodiments, that jaw member 704 and ablation members 712, 714 could alternatively be configured in any other suitable shape, size or configuration to ablate in other patterns on heart 140. Additionally, device 700 may be moved to a variety of positions to ablate multiple patterns in multiple locations on the epicardial tissue.

Figure 9:
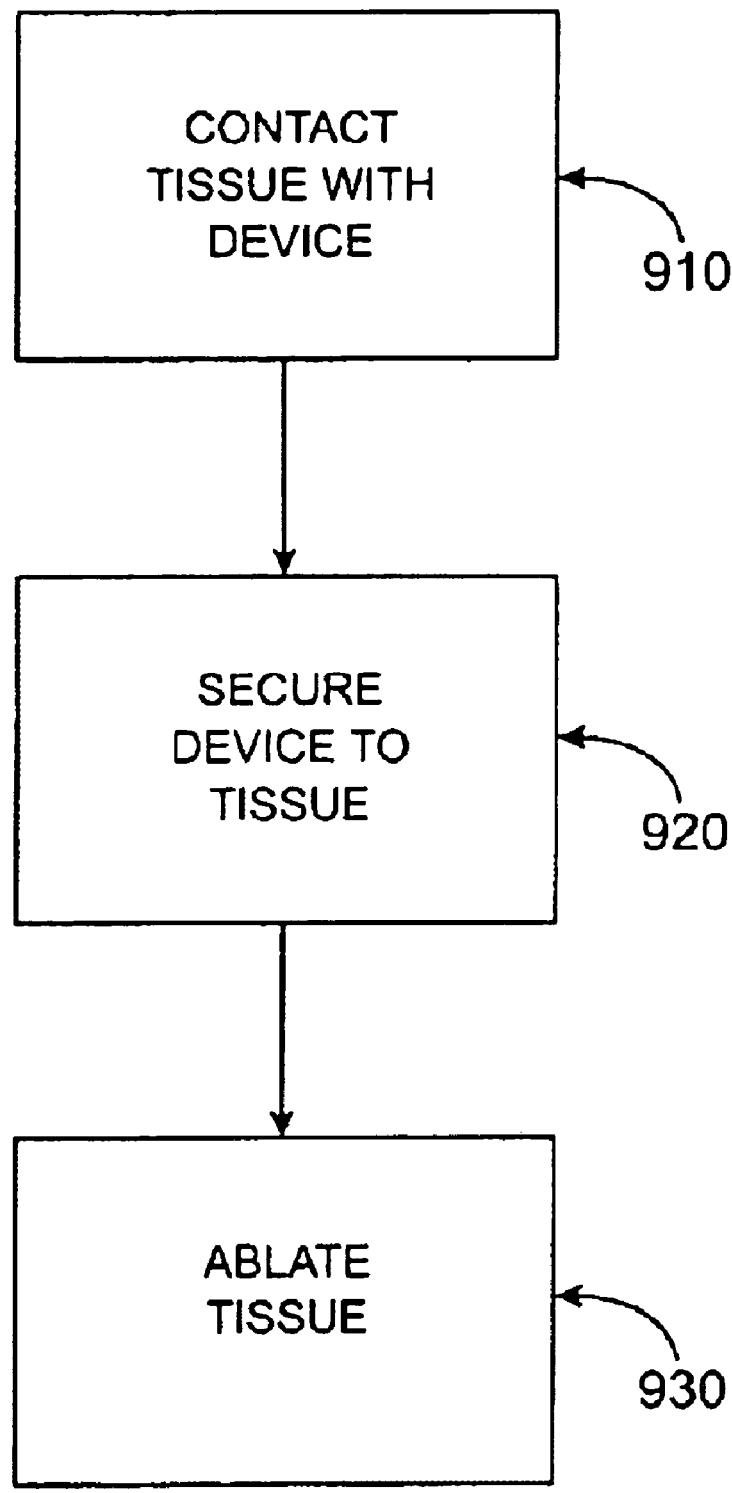
FIG. 9 is a block diagram of a method for ablating tissue according to one embodiment of the invention.

With reference now to FIG. 9, a method for ablating cardiac tissue, such as epicardial tissue, suitably includes contacting cardiac tissue with an ablation device 910, securing the device to the tissue 920 and ablating at least a portion of the contacted, secured tissue 930. Various embodiments of the invention will utilize additional steps or sub-steps of these three basic steps, but it should be emphasized that any additional steps or variations are optional. For example, in some embodiments, contacting the cardiac tissue 910 is preceded by advancing the device into the patient through a minimally invasive introducer device. Contacting the device with the tissue 910 may include positioning the device using a positioning arm or other positioning device. In some embodiments, securing the device to the tissue 920 may also comprise invaginating a portion of epicardial tissue partially within one or more suction apertures and/or may include using one or more suction apertures to dissect through fatty tissue disposed over epicardium. Securing the device 920 may also involve securing with enough force to allow stabilization and/or positioning of the heart itself. And ablation of epicardial tissue 930 may involve ablation in any location or pattern as described above with reference to the inventive devices. Therefore, the descriptions of various methods provided herein are offered for exemplary purposes only and should not be interpreted to limit the scope of the invention as described in the claims.

Other aspects of a method for ablating epicardial tissue may include imaging the epicardial tissue and an area surrounding the tissue to be ablated, using a visualization device. Such a device may be coupled with the ablation device or may be a separate imaging device. In some embodiments, an insufflation device may be inserted between the epicardium and the pericardium and insufflation fluid or gas may be introduced to form a space between the epicardium and pericardium. The space may be used to enhance visualization, allow for freer manipulation of devices near the site for ablation and the like. Another aspect may include sensing ablation of epicardial tissue with one or more sensors, as described above. In some embodiments, tissue may optionally be cooled via a cooling member and/or irrigation of fluid into contact with the tissue. Finally, the actual ablation of epicardial tissue may be accomplished with any suitable ablation member and form of energy, including RF, thermoelectric, cryogenic, microwave, laser, ultrasound or the like. In one embodiment, ablation is achieved and/or enhanced by delivery of one or more drugs to the tissue.

The method may further include the steps of using visual and audible cues to verify the ablation device is adhered to tissue. For example the user can hear a suction sound or 'whistle' when the suction has been activated and the ablation device is not correctly adhered. Also, the user can hear vacuum pump elevate as vacuum increases. In some embodiments, the user can visually observe the tissue contacting member collapse when the ablation device is correctly adhered and suction is activated.

Figure 10:
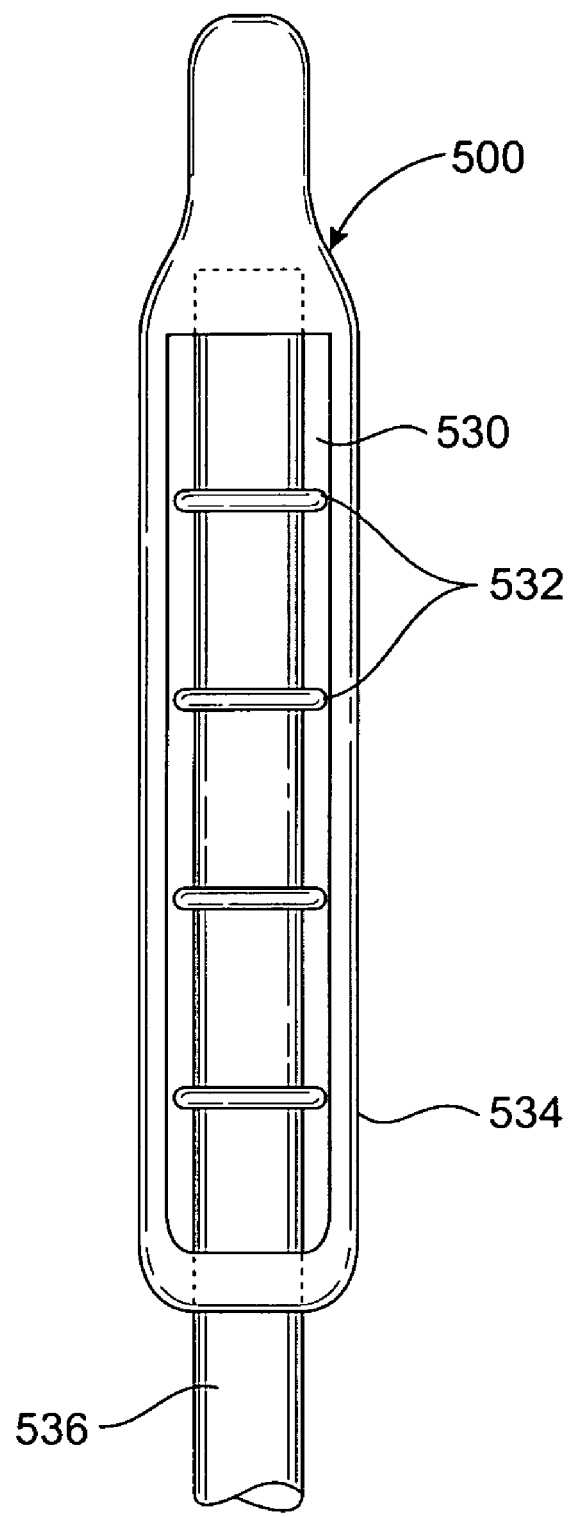
FIG. 10 is an embodiment of the invention including an elongated tissue contact member, built in accord with the invention.

In general, any number of suction pods may be used in the invention, and the number used may depend on the procedure that is to be performed. For example, FIG. 10 shows an embodiment of the ablation device 500 including a tissue contact member 534 with only a single elongated suction pod 530. In this embodiment, the suction pod 530 extends a selected length of the ablation member 536 and includes graspers 532 to hold the ablation member 536 within the suction pod 530. Any desired mechanism for holding the ablation member 536 may be used. For example, the graspers 532 may be narrow channel sections in which the ablation member 536 may be snapped into place, or the graspers 532 may be loops through which the ablation member 536 is slid into place.

In further embodiments, the ablation device may be configured to allow the ablation member to extend beyond the edge of the tissue contacting member to allow for ablation to occur outside of the region covered by the tissue contacting member.

Figure 11:
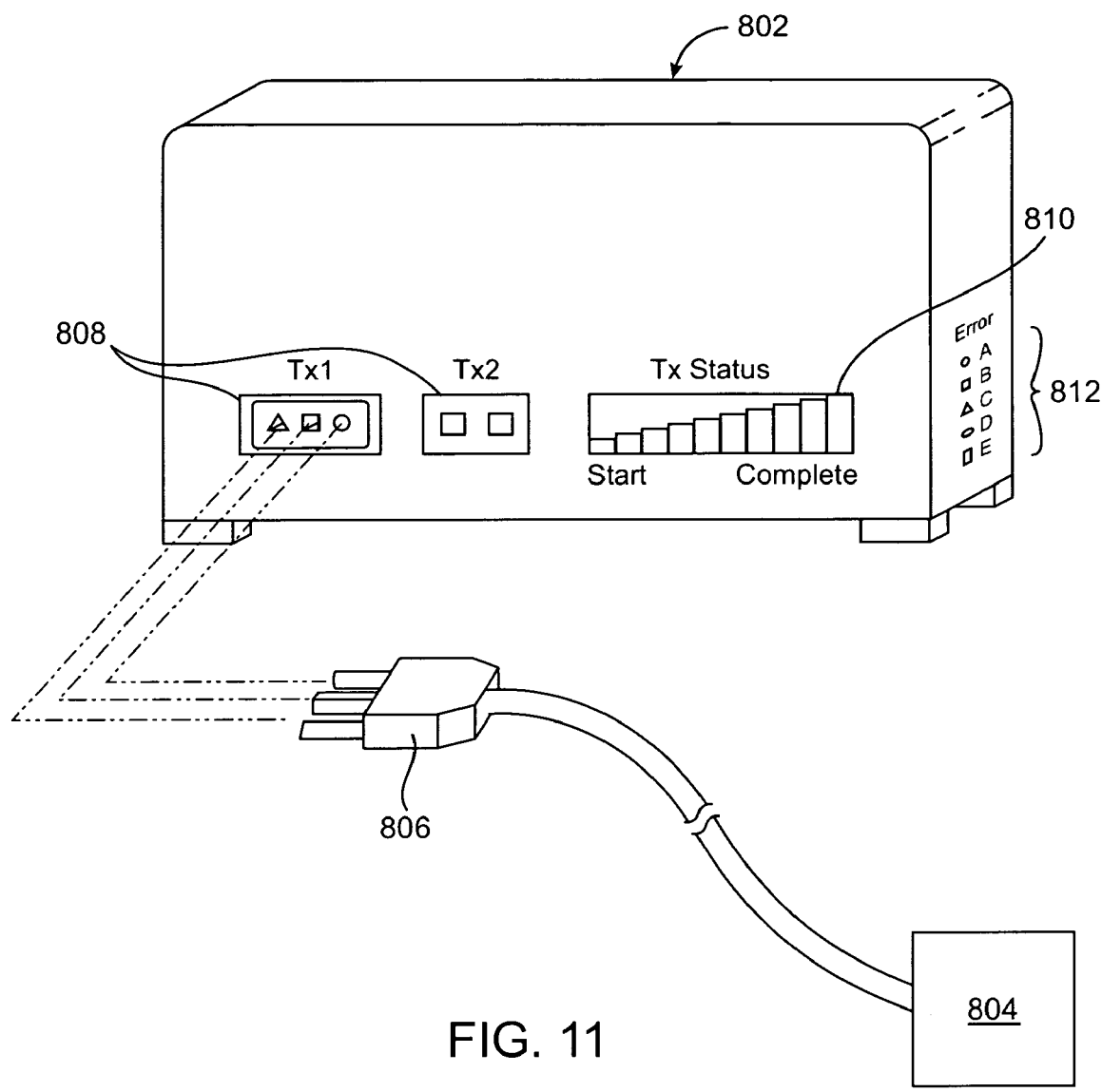
FIG. 11 is an example embodiment of a power source built in accord with the invention.

Referring to FIG. 11, an ablation system 800 built in accord with the invention is shown including an ablation energy source 802 for providing power to the ablation device 804. The ablation energy source 802 shown is an RF energy source particularly suited for use with ablation apparatus as described herein, but is not limited to such use. Other kinds of ablation energy sources and ablation devices may be useable in the invention.

In some embodiments, the ablation system 802 is configured to recognize the kind of ablation device connected by including keyed plugs. Thus, in this embodiment, the energy source 802 includes sockets 808 configured with specialized shapes to accept only plugs which are manufactured with the matching shape. The Energy source 802 is configured with predetermined settings appropriate for the kind of device that is accepted by that socket shape. More than one socket 808 and associated pre-determined setting may be included. Ablation devices 804 to be used with the energy source will be provided with a plug shape (for example plug 806 on ablation device 804) to be received in on of the sockets 808 that will provide the appropriate energy requirements.

In another embodiment, the ablation system of the invention includes apparatus for recognizing the kind of device that has been coupled to the energy source and for automatically adjusting various settings to accommodate the detected device. Examples include but are not limited to known logic chip device recognition systems and RFID systems. This embodiments can be used in combination with keyed plugs as described above.

In another embodiment, the ablation system will provide information useful to the treating physician and/or other medical personnel, about the progress of treatment and the status of the equipment. For example, the system may include a feedback loop to self monitor the energy delivery of the system and automatically turn off the delivery of energy once the treatment is complete. The feedback mechanism may include electrical sensors, thermoelectric sensors, microchips, thermistors, thermocouples, Doppler sensors, microwave sensors, and ultrasonic sensors, or thermal energy emitting and receiving devices. In some embodiments, the treatment progress is monitored and indicated with a visual display such as example visual displays 810 and 812. In these embodiments the sensors may be in communication with processors or other control devices included in the energy source, which can analyze and display the data received from the sensors.

In still further embodiments, the ablation device may include more electrodes that are available on the energy source. This allows ablation device construction to facilitate longer ablations by utilizing multiple connections to energy source. For example, In one embodiment, the ablation device includes a plurality of electrodes, and the energy source includes less electrodes than the ablation device. In this case, the ablation device preferably includes at least two plugs, with each plug providing power to a subset of the plurality of electrodes on the ablation device. By connecting the first plug of the ablation device to the energy source, applying ablation energy to the tissue, unplugging the first plug from the energy source, plugging the second plug of the ablation device in to the energy source, and applying ablation energy to the tissue, all of the ablation elements can be activated. More specifically, if an energy source includes seven electrodes couple to a single plug to power seven ablation segments on the ablation device, the ablation device may include fourteen separate ablation segments. Each set of seven ablation segments would couple to a separate plug. In use, the first plug is inserted into the energy source and the first set of seven ablation segments is activated. Upon completion of treatment, possibly without moving the ablation device, a second region may be ablated by removing the first plug and inserting the second plug to activate the next seven ablation segments on the ablation device. This embodiment can result in a smaller less expensive energy source that is still capable of powering a long ablation device.

In one embodiment, a method first includes advancing an ablation device through a minimally invasive introducer device into a patient and to a location for ablating epicardial tissue. The device is then contacted with the epicardial tissue and positioned on the tissue with a positioning arm or other device inserted through the same or a separate minimally invasive introducer or incision. Positioning device, in some embodiments, may be a flexible, rigidifying positioner which allows for positioning and then stabilizing with the same device. The ablation device may be placed in any suitable location for ablating epicardial tissue. In one embodiment, for example, ablation device will contact tissue at least partially encircling two pulmonary veins, such as the right superior and right inferior pulmonary veins. The ablation device may contact epicardial tissue directly adjacent the bases of the veins but may be configured to maintain a safe distance between the ablation member on the device and the actual veins.

Once the epicardial tissue is contacted, the device may be secured to the tissue by securing means, such as suction or adhesive. In fact, the device may be secured to the tissue sufficiently in some embodiments to allow the heart to be stabilized and/or positioned using the device and a positioner. For example, a beating heart may be stabilized to reduce or eliminate motion during an ablation procedure or may be pulled, turned or otherwise moved into an advantageous position for ablating, visualizing or treating the heart. Suction force may also be supplied in sufficient strength to dissect through a layer of adipose tissue overlying the epicardial tissue, which may provide improved contact of an ablation member with the epicardial tissue. Once the tissue is secured, at least a portion of the tissue may be ablated by delivering energy to an ablation member (or members) on the device. As already described in detail, such energy may include any suitable energy and may additionally or alternatively include one or more ablative drugs. After ablation, tissue may be cooled via cooling means and/or ablation of tissue may be sensed with one or more sensors. When an ablative procedure is complete, the device may be removed and placed in another location on the heart for an additional procedure or may be removed from the patient altogether.

Figure 12A:
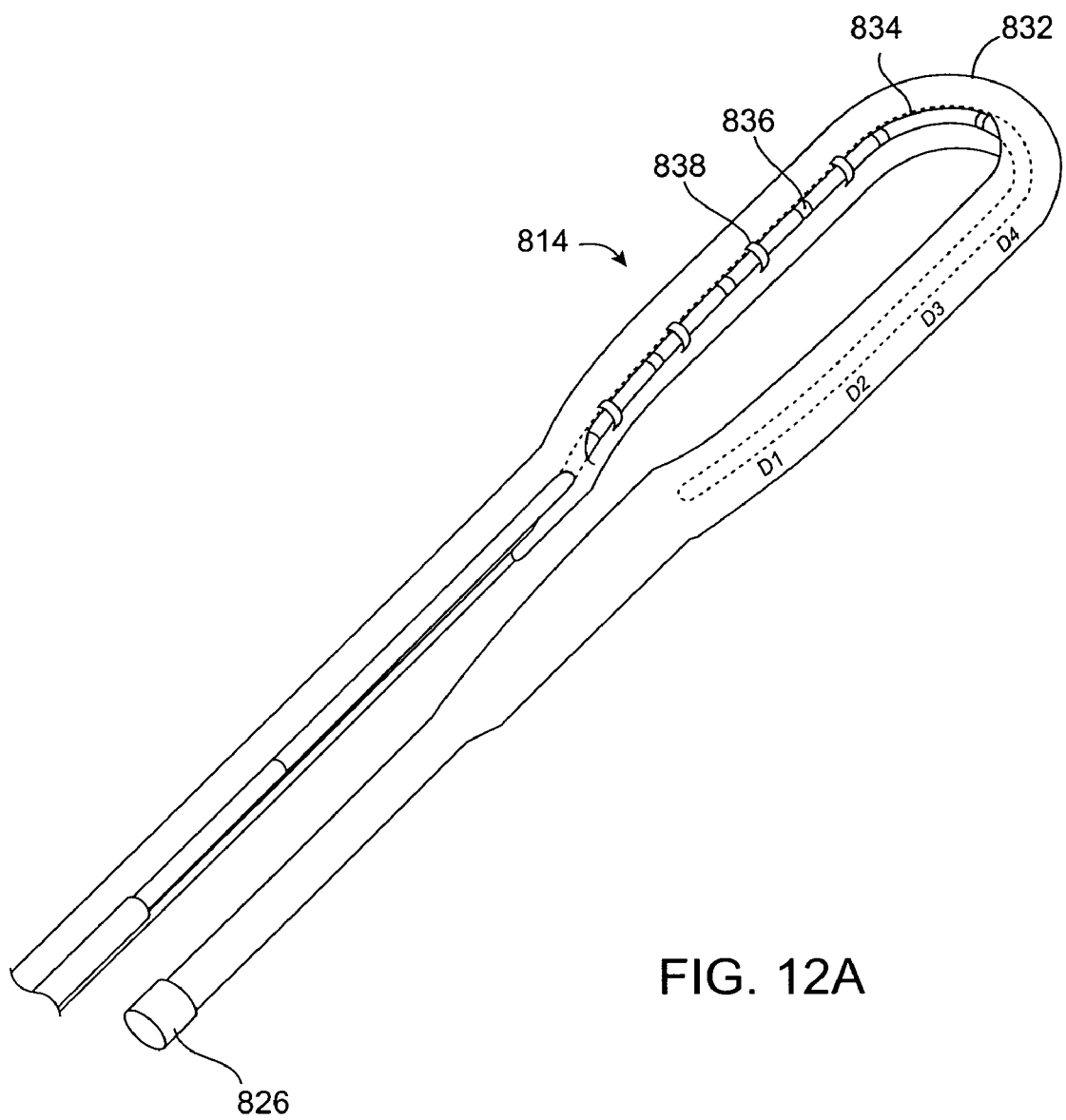
FIGS. 12a and 12b is an example of an ablation device in accord with the invention, and an introducer for use with the ablation device.
Figure 12B:
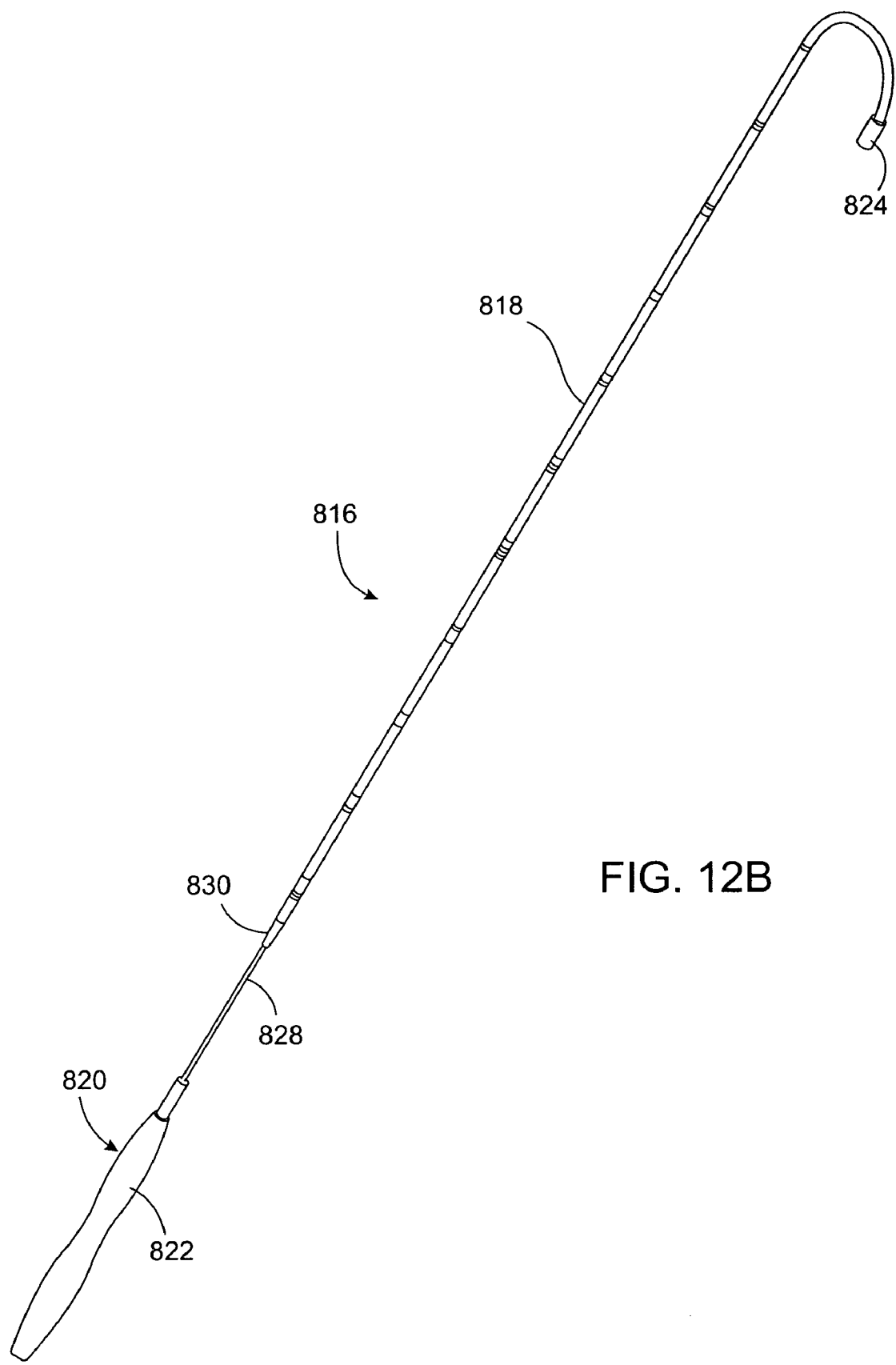

Another apparatus and method of the invention includes the following. Referring to FIGS. 12a and 12b. In some embodiments, the ablation device 814 may be deployed using an introducer 816 (best seen in FIG. 12b). The introducer 816 in this embodiment comprises a tube 818 that is pre-bent into a J shape. An obturator 820 with a handle 822 and a shaft 828 which is inserted in to the tube 818 with the shaft 828 extending substantially through the length of the tube 818. When the obturator 820 is removed, the tube 818 returns to its pre-bent J shape.

A distal end 824 of introducer 816 has a designate region for grasping. A selected instrument may be introduced through a the same or a second incision to grasp the distal end 824 of the introducer 816 to pull the distal end 824 of the introducer 816 outside the body of the patient. The distal end 826 of the ablation device 814 of FIG. 12a is attached to the proximal end 830 of the introducer 816. The introducer 816 is then withdrawn until the ablation device 814 is properly positioned.

In the example embodiment of the ablation device 814 seen in FIG. 12a, the ablation device 814 includes a tissue contacting member 832 including a single suction pod 834. An ablation member 836 extends through the length of the tissue contacting member 832 and includes graspers 838 to hold the ablation member 836 within the suction pod 832. Once the treatment is complete, the ablation device 814 may be decoupled from the energy source and pulled out.

An example method for using the invention described above includes the following steps. An introducer is advanced through a first incision into the transverse sinus cavity with obturator fully inserted. At desired area near the pulmonary veins, obturator is withdrawn and the which allows the introducer to assume its pre-formed J shape reaching round the pulmonary veins, possibly also guided by contact with the pericardium. The introducer is preferably long enough to be inserted from thoracotomy into transverse sinus cavity around the pulmonary veins and out through the oblique sinus and out through the same or a different thoracotomy. Another instrument is advanced through the same or different thoracotomy to grasp the distal end of the introducer. The introducer is pulled around the pulmonary veins until the distal end is outside the body of the patient. At this point, both the proximal and distal ends of the introducer are preferably outside the body of the patient.

The proximal end of introducer is attached, possibly with luer fitting, to the distal end of an ablation device. Indication markers and lines on introducer and on the ablation device can be used to assist the user in properly positioning the ablation device. In a preferred embodiment, circumferential indication markers on the introducer are used as depth measurements, and an indication stripe on the surface of the introducer are aligned with similar markings on the ablation device to insure that the ablation device will be facing properly when inserted.

In this method, the introducer preferably has torsional rigidity to facilitate steerability. Further, the introducer is preferably a highly visible color for endoscopic visualization and distinguishing from natural anatomical colors.

Once the ablation device is in position, suction is applied to adhere the ablation device to the tissue surrounding the pulmonary veins. Ablation energy is applied. Once treatment is complete, the ablation device can be removed.

Another method of the invention includes a method of performing a 'hybrid' medical procedure comprising creating a continuous lesion encircling or partially encircling the pulmonary veins to electrically isolate the pulmonary veins during a surgical procedure and creating additional ablation lesions in the left and/or right atrium, vena cava, endocardium to the mitral valve annulus, or along the left atrial appendage to create a Maze-like lesion set for treatment of atrial fibrillation.

Figure 14:
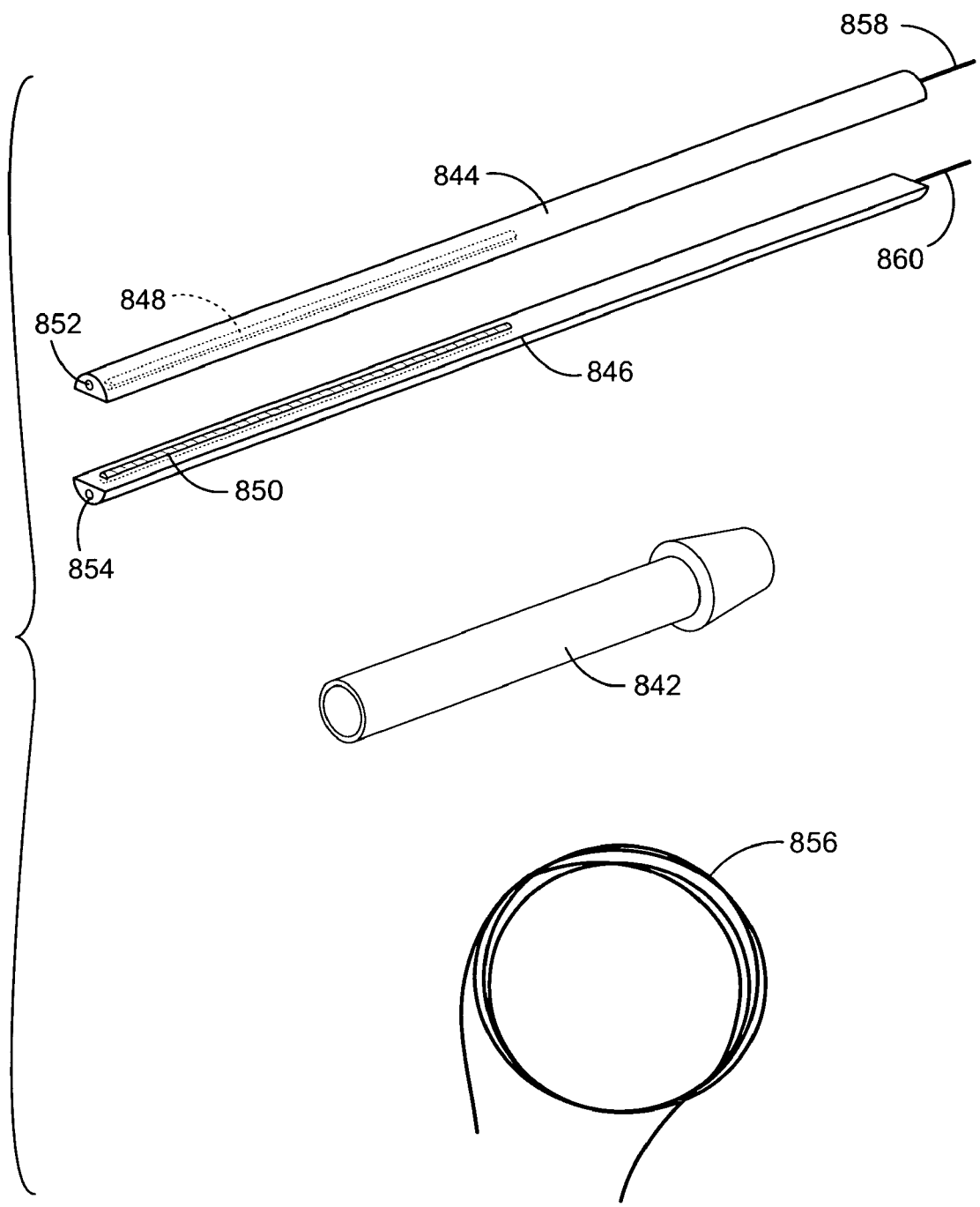
FIG. 14 is an exploded view showing the components of the ablation device of FIG. 13.

FIG. 13 is an assembly drawing of an ablation device 840 that is configured to be used through an introducer or trocar cannula 842. FIG. 14 is an exploded view showing the components of the ablation device 840 of FIG. 13. A thoracic access port is created between the ribs for insertion of the ablation device 840. An introducer or trocar cannula 842 is placed through the thoracic access port. The ablation device 840 includes two elongate flexible polymeric clamp jaws 844, 846. The outer surfaces of the clamp jaws 844, 846 are rounded. The inner surfaces of the clamp jaws 844, 846 are flat with an ablation electrode 848, 850 on each of the clamp jaws 844, 846. Preferably, the ablation electrodes 848, 850 are embedded within the flat inner faces near the distal ends of the clamp jaws 844, 846. The ablation electrodes 848, 850 may be configured as simple wires embedded in the flat inner faces of the clamp jaws 844, 846. Alternatively, each of the ablation electrodes 848, 850 may be configured with at least one, and up to about ten, electrode segments. For flexibility, the electrode segments are preferably configured as helically cut cylinders of metal hypodermic tubing or the like embedded in the flat inner faces of the clamp jaws 844, 846. The use of a flexible or deformable conductive material in the ablation electrodes 848, 850 provides evenly distributed contact pressure and lesion depth over a variable thickness portion of tissue. Optionally, a mesh coating covers the electrode segments to prevent contact of the ground and active electrode segments if tissue is not between them. The coils are typically dipped in saline before use to insure conductivity. Optionally, the electrode segments may be individually addressable as in some of the embodiments described above. A connection wire 858, 860 extends from each of the ablation electrodes 848, 850 to the proximal end of the clamp jaws 844, 846 to allow connection to an ablation power source. As the clamp jaws 844, 846 are advanced distally though the introducer or trocar cannula 842, they open up, with the ablation electrodes 848, 850 on the flat inner faces separating, the faces being maintained parallel, and separation distance up to 5 cm. As the clamp jaws 844, 846 are retracted proximally through the port, the introducer or trocar cannula 842 exerts forces on the outer faces of the clamp jaws 844, 846 causing them to close around the tissue. Preferably, the clamp jaws 844, 846 are configured to close around the tissue with the ablation electrodes 848, 850 and the flat inner faces in parallel alignment. Alternatively, the clamp jaws 844, 846 can be configured so that the distal ends close around the tissue first, to prevent the tissue from being squeezed out from between the clamp jaws 844, 846 as they close. Optionally, one or both of the clamp jaws 844, 846 may include a tooth or other grasping feature near the distal end to prevent the tissue from being squeezed out from between the clamp jaws 844, 846 as they close. The length of jaws may be up to 60 cm or more to facilitate remote insertion.

Optionally, one or both of the clamp jaws 844, 846 could be malleable or include a malleable member to allow reconfiguring of the clamp jaws 844, 846 for accessing a desired target tissue. The malleable portion may extend the full length of the clamp jaws 844, 846 or it may be limited to a proximal, distal or intermediate portion of the clamp jaws 844, 846. Alternatively or in addition, one or both of the clamp jaws 844, 846 could also have one or more hinge joints or articulating links to facilitate optimal positioning of the ablation device. For example, a remotely steerable hinge joint may be located on each of the clamp jaws 844, 846 just proximal to the ablation electrodes 848, 850 to facilitate accessing a desired target tissue, while maintaining the ablation electrodes 848, 850 in an approximately parallel alignment. In alternate configurations, the clamp jaws 844, 846 may be joined together, e.g. hinged or molded as one piece in a V-shaped or Y-shaped configuration. Alternatively or in addition, the clamp jaws 844, 846 may be curved to cause the inner surfaces with the ablation electrodes 848, 850 to separate as the clamp jaws 844, 846 advance distally trough the introducer or trocar cannula 842. Preferably, the clamp jaws 844, 846 will have a central lumen 852, 854 to facilitate a guidewire 856 that can be steerable going out of one jaw and into another. This could act to lasso a tissue structure to be brought into the clamp jaws 844, 846.

Preferably, the ablation electrodes 848, 850 on the clamp jaws 844, 846 are configured for bipolar ablation. When applying ablation energy through the ablation electrodes 848, 850, one electrode may act as an active electrode, while the other acts as a passive ground. Alternatively, the ablation electrodes 848, 850 may both act as active electrodes by applying opposite voltages or polarity of alternating (e.g. radio frequency) current to the two ablation electrodes 848, 850. Typically, another ground electrode will be applied to an external surface of the patient for safety.

The apparatus can be used to create any lesion, with one jaw endocardial and the other epicardial. In a preferred method, the apparatus is used with both jaws positioned epicardially to isolate one or more electrical focii (pulmonary veins) or peninsula-like tissue structure (such as the left or right atrial appendage). The apparatus can be used to create one or more lesions along the atrial base of the pulmonary veins, thereby electrically isolating the pulmonary veins from the left atrium.

As described above, thermal imaging can be used to visualize the energy emission during an ablation procedure using any of the ablation devices described herein. In addition, thermal imaging can be used as a development tool for ablation probes. Thermal images of the ablation procedure in vitro or in vivo allow optimization of the device geometry and energy settings. For example, thermal imaging has been used to optimize energy settings of ablation devices in an epicardial beating heart heat sink model. The energy settings thus established were subsequently used in vivo to achieve the desired depth of heat penetration in tissue during actual ablation procedures.

Conduction Block Verification Probe

Figure 15:
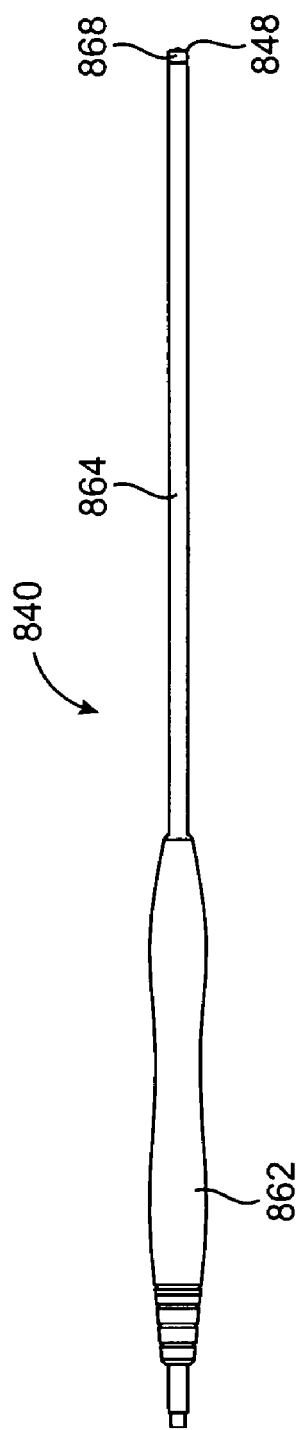
FIG. 15 illustrates a conduction block verification probe in accord with the invention.
Figure 17:
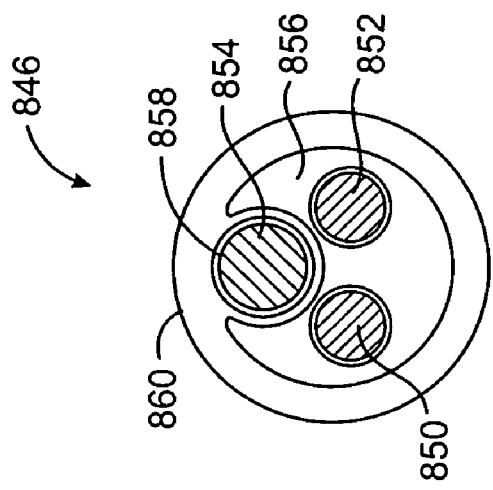
FIG. 17 shows a cross section of the conduction block verification probe shaft.
Figure 16:
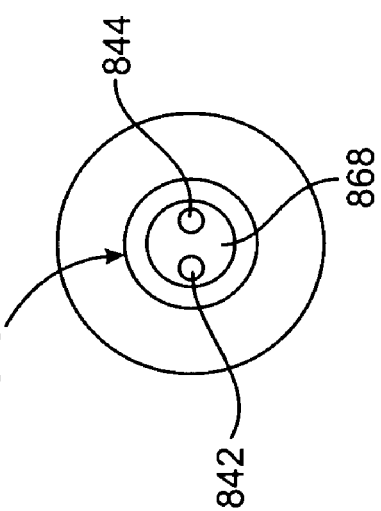
FIG. 16 shows an enlarged distal end view of the conduction block verification probe.

The present invention also encompasses apparatus and methods to verify electrical conduction block across ablation lesions. The apparatus and methods may be used in conjunction with any of the ablation devices and methods described herein, or others known in the art, to verify the effectiveness of the ablation procedure in creating an electrical conduction block across the cardiac tissue. The apparatus includes a conduction block-verification probe or temporary bipolar pacing probe 840. FIG. 15 illustrates a conduction block verification probe 840 in accord with the invention. FIG. 16 shows an enlarged distal end view of the conduction block verification probe 840. FIG. 17 shows a cross section of the shaft 846 of the conduction block verification probe 840. The conduction block verification probe 840 is a single use, hand held device used for temporary pacing of tissue. The probe has two integrated pacing electrodes 842, 844 at the distal end 848. These electrodes 842, 844 contact the tissue. Wires 850, 852 extend through the shaft 846 and terminate in an electrical connector (866 in FIGS. 18-19, 876 in FIGS. 20-21) configured to connect the electrodes 842, 844 to a bipolar pacing generator or ECG (not shown). An electrical pulse is then transmitted to stimulate tissue. In the preferred embodiment the electrical pulse is at a rate higher than the intrinsic atrial or ventricular contraction rate (heart rate). A measurement of the minimum voltage or amperage required to excite tissue (the pacing threshold), above the intrinsic excitation rate, will be recorded prior to and following completion of ablation lesions aimed to isolate specific regions of the heart.

Preferably, the conduction block verification probe 840 is constructed with a malleable shaft 846 connected to an ergonomic handle 862. The malleable shaft 846 is bendable to 90 degrees without buckling or kinking. The malleable shaft 846 will preferably have a working length of approximately 8 inches (approximately 20 cm) as measured from the handle 862 to the distal end 848 and an external diameter of approximately 0.20 inches (approximately 5 mm) or less. The malleable shaft 846 will preferably extend through the handle 862 and extend proximally from the handle 862 by approximately 0.2 to 0.5 inches. As shown in cross section in FIG. 17, the malleable shaft 846 is constructed with a dual lumen extruded polymer tube 860. Suitable materials for the dual lumen extruded polymer tube 860 include, but are not limited to, polypropylene, polyethylene, polyurethane, nylon, and copolymers or composites thereof. A malleable wire 854 with a diameter of approximately 0.062 inches extends through one lumen 858 of the dual lumen tube 860 through the entire length of shaft 846 and handle 862. Suitable materials for the malleable wire 854 include, but are not limited to, annealed stainless steel, copper, lead, tin and aluminum. Insulated wires 850, 852 extend through the other lumen 856 of the dual lumen tube 860 and through a cable 864 with a length of approximately 36 inches that extends proximally from the handle 862.

The conduction block verification probe 840 is capable of reaching the left atrium adjacent to the pulmonary veins from a port or thoracotomy in the left or right chest or a mid line sternotomy. The distal end 848 of the conduction block verification probe 840 will be applied in direct contact with the epicardium of the heart and transmits electrical energy to electrically stimulate the heart while connected to an external pulse generator. Preferably, the conduction block verification probe 840 will be positioned using direct or endoscopic visualization of the tissue surface. The pacing electrodes 842, 844 are preferably configured as two ball-tip electrodes approximately 0.062 inches (approximately 1.5 mm) in diameter held by an insulating spacer 868 attached to the distal end 848 of the shaft 864. Suitable materials for the insulating spacer 868 include, but are not limited to, silicone, polypropylene, polyethylene, polyurethane, nylon, and other medical grade polymers. The electrodes 842, 844 should be spaced with a separation of approximately 2 mm. The electrodes 842, 844 should be exposed on the distal end of the device with a minimum extension of 1 mm from the insulating spacer 868.

The electrical connectors (866 in FIGS. 18-19, 876 in FIGS. 20-21) of the conduction block verification probe 840 are configured to be compatible with extension cables that connect to various external pulse generators and ECG recorders, respectively. The conduction block verification probe 840 is capable of transmitting electrical pacing pulses of variable amplitude up to 20 mA or 10V in amplitude to pace the heart above normal sinus rhythm, preferably up to 200 BPM to the target anatomical area of the epicardium. The conduction block verification probe 840 is also capable of passively transmitting electrical pulses from the heart to an ECG recorder.

Figure 18:
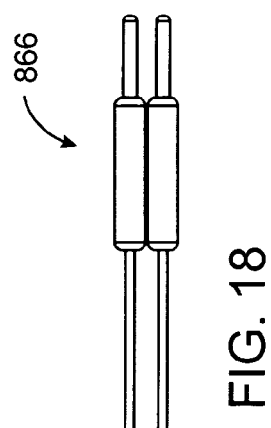
FIG. 18 shows a bipolar electrical connector for use with the conduction block verification probe.
Figure 19:
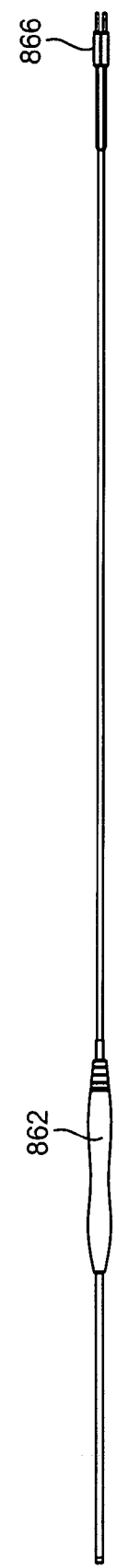
FIG. 19 is an assembly drawing of a conduction block verification probe in a configuration for temporary pacing of the left atrium.

FIG. 18 shows a bipolar electrical connector 866 for connecting the conduction block verification probe 840 to a bipolar pacing pulse generator. FIG. 19 is an assembly drawing of a conduction block verification probe 840 with the bipolar electrical connector 866 in a configuration for temporary pacing of the left atrium. The conduction block verification probe 840 will be used to verify electrical conduction block across ablation lesions, an indication of lesion continuity and electrical isolation of specific regions. The conduction block verification probe 840 can be used after creating a set of lesions on the epicardium of the left atrium encircling the pulmonary veins using surgical, interventional cardiology or electrophysiology treatments for Atrial Fibrillation to determine if electrical conduction block was achieved. In the preferred method the conduction block verification probe 840 will be used to pace the left atrium by contacting the left atrium both inside and outside an encircling lesion around the pulmonary veins. If significantly more voltage or current is required to pace the heart from inside the encircling lesion as opposed to outside, an inference of electrical isolation of the pulmonary veins can be made. This will be used to assess electrical isolation of several regions of the heart across ablation lesions during surgical treatment of atrial fibrillation, open or minimally invasively, epicardially or endocardially. The pulse generator will supply a higher than normal pacing rate and electrical impulse at variable amplitudes. The device will contact the left atrium within the encircling lesion adjacent to the pulmonary veins and paced to determine if electrical isolation or block was successful. If block is not successful, then the impulse will be captured outside the encircling lesion and pacing of the entire heart will take place.

Figure 20:
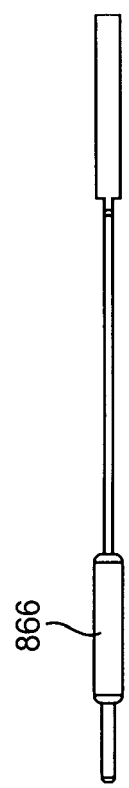
FIG. 20 shows a unipolar electrical connector for use with the conduction block verification probe.
Figure 21:
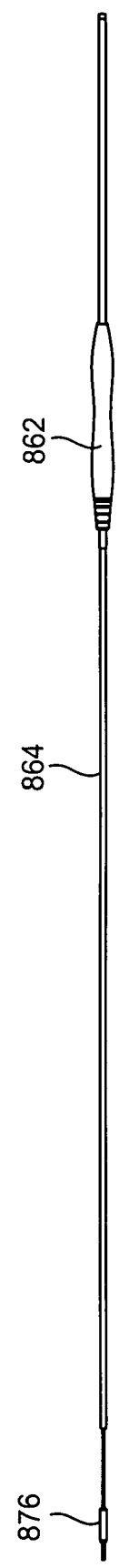
FIG. 21 is an assembly drawing of a conduction block verification probe in a configuration for ECG sensing.

FIG. 20 shows a unipolar electrical connector 876 for connecting the conduction block verification probe 840 to an ECG recorder via a compatible extension cable. FIG. 21 is an assembly drawing of the conduction block verification probe 840 with the unipolar electrical connector 876 in a configuration for ECG sensing. In this configuration, the conduction block verification probe 840 may optionally be constructed with only a single electrode at the distal end of the device. ECG sensing on the epicardial surface may be used to help verify the conduction block and/or to help locate and map signal pathways in the tissue that have not been adequately ablated. Alternatively, this configuration of the conduction block verification probe 840 can be also used for unipolar pacing of the heart. Alternatively, the bipolar configuration of the conduction block verification probe 840 shown in FIGS. 18-19 can be used for ECG sensing by connecting only one of the electrical connectors 866 to the ECG recorder.

While the present invention has bee shown and described with reference to various embodiment thereof, the above and other changes in form and detail may be made without departing from the spirit and scope of the invention as defined in the following claims.

What is claimed is:

1. A bipolar conduction block verification probe comprising:
    an elongate probe shaft having a proximal end and a distal end;
    a first pacing electrode and a second pacing electrode exposed on a distal-facing surface at the distal end of the elongate probe shaft; and a first wire connected to the first pacing electrode and extending through the elongate probe shaft to a first electrical connector configured for connection to an external bipolar pacing pulse generator and a second wire connected to the second pacing electrode and extending through the elongate probe shaft to a second electrical connector configured for connection to the external bipolar pacing pulse generator,
    wherein the elongate probe shaft includes a malleable member capable of being bent to a desired configuration and maintaining the desired configuration, wherein the elongate probe shaft is configured with a polymer tube having a first lumen and a second lumen, and wherein the malleable member is an elongated member that extends through the first lumen and the first wire and the second wire extend through the second lumen.

2. The bipolar conduction block verification probe of claim 1, further comprising:
    an external bipolar pacing pulse generator connected to the first pacing electrode and the second pacing electrode through the first electrical connector and the second electrical connector, wherein the external bipolar pacing pulse generator is capable of transmitting electrical pacing pulses of variable amplitude up to 20 mA and 10 V in amplitude to pace the heart above normal sinus rhythm up to 200 beats per minute.

3. The bipolar conduction block verification probe of claim 1, further comprising an insulating spacer separating the first pacing electrode and the second pacing electrode.

4. The bipolar conduction block verification probe of claim 3, wherein the first pacing electrode is configured with a first ball-shaped tip extending approximately 1 mm from a distal surface of the insulating spacer and the second pacing electrode is configured with a second ball-shaped tip extending approximately 1 mm from the distal surface of the insulating spacer, with the first ball-shaped tip spaced apart from the second ball-shaped tip by approximately 2 mm.

* * * * *